United States Patent
Jimenez et al.

(10) Patent No.: US 8,727,652 B2
(45) Date of Patent: May 20, 2014

(54) ORAL CARE SYSTEM, KIT AND METHOD

(75) Inventors: Eduardo Jimenez, Manalapan, NJ (US); Sharon Kennedy, Randallstown, MD (US); Robert Moskovich, East Brunswick, NJ (US); John Gatzemeyer, Hillsborough, NJ (US); Alan Sorrentino, Cranbury, NJ (US); Michael Rooney, Millburn, NJ (US); Joseph Fattori, East Sandwich, MA (US)

(73) Assignee: Colgate-Palmolive Company, New York, NY (US)

( * ) Notice: Subject to any disclaimer, the term of this patent is extended or adjusted under 35 U.S.C. 154(b) by 347 days.

(21) Appl. No.: 13/254,440

(22) PCT Filed: Dec. 22, 2010

(86) PCT No.: PCT/US2010/060874
§ 371 (c)(1),
(2), (4) Date: Sep. 1, 2011

(87) PCT Pub. No.: WO2011/079028
PCT Pub. Date: Jun. 30, 2011

(65) Prior Publication Data
US 2012/0034016 A1 Feb. 9, 2012

Related U.S. Application Data

(63) Continuation-in-part of application No. PCT/US2009/069408, filed on Dec. 23, 2009, which is a continuation-in-part of application No. PCT/US2009/069402, filed on Dec. 23, 2009.

(60) Provisional application No. 61/410,514, filed on Nov. 5, 2010, provisional application No. 61/423,397, filed on Dec. 15, 2010, provisional application No. 61/423,414, filed on Dec. 15, 2010, provisional application No. 61/423,435, filed on Dec. 15, 2010, provisional application No. 61/423,449, filed on Dec. 15, 2010.

(51) Int. Cl.
*A46B 11/04* (2006.01)
*A46B 11/00* (2006.01)

(52) U.S. Cl.
CPC .................. *A46B 11/0024* (2013.01)
USPC ........................... 401/277; 401/174; 401/172

(58) Field of Classification Search
CPC .......... A46B 11/0024; A46B 11/0027; A46B 11/0065; A46B 2200/1066
USPC ......................................... 401/277, 171–175
See application file for complete search history.

(56) References Cited

U.S. PATENT DOCUMENTS

| 64,732 A | 5/1867 | Wylie |
| 261,456 A | 7/1882 | Hoffman |

(Continued)

FOREIGN PATENT DOCUMENTS

| EP | 1506726 | 2/2005 |
| FR | 850458 | 12/1939 |

(Continued)

OTHER PUBLICATIONS

International Search Report and Written Opinion in International Application No. PCT/US10/60881 mailed May 16, 2011.

(Continued)

*Primary Examiner* — David Walczak
*Assistant Examiner* — Jennifer C Chiang
(74) *Attorney, Agent, or Firm* — Ryan M. Flandro

(57) ABSTRACT

An oral care system, such as a toothbrush having a detachable dispenser containing an oral care material. In one embodiment, the dispenser may include a housing; an internal reservoir for containing a fluid and a dispensing orifice for dispensing the fluid; a first cam surface, the first cam surface being non-rotatable with respect to the housing; a reciprocator comprising an actuator, a drive screw, and a second cam surface, the reciprocator being rotatable with respect to the housing; an elevator forming a transverse end wall of the reservoir, the elevator being non-rotatable with respect to the housing and threadily coupled to the drive screw; wherein rotation of the actuator causes the elevator to (1) axially advance, and (2) axially reciprocate.

34 Claims, 13 Drawing Sheets

(56) References Cited

U.S. PATENT DOCUMENTS

| | | |
|---|---|---|
| 1,244,324 A | 10/1917 | Hackley |
| 1,292,416 A | 1/1919 | Auld |
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,746,474 A | 2/1930 | Hogner |
| 1,913,528 A | 6/1933 | White |
| 1,975,723 A | 10/1934 | Johnssen |
| D134,723 S | 1/1943 | Riksheim |
| 2,356,874 A | 8/1944 | Nageotte |
| 2,437,769 A | 3/1948 | Traylor |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,637,060 A | 5/1953 | Cowan |
| 2,670,881 A | 3/1954 | Sjoblom |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 7/1957 | Barron |
| 2,885,110 A | 5/1959 | Tregilgas |
| 2,885,116 A | 5/1959 | Tregilgas |
| 3,108,687 A | 10/1963 | Dayton |
| 3,148,684 A | 9/1964 | Keeler |
| 3,181,539 A | 5/1965 | Aston |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,986,645 A | 10/1976 | Baldwin et al. |
| 4,275,750 A | 6/1981 | Clark |
| 4,277,194 A | 7/1981 | Smith |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,641,766 A | 2/1987 | Vlasich |
| 4,655,372 A | 4/1987 | Ross et al. |
| 4,659,327 A | 4/1987 | Bennett et al. |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,826,341 A | 5/1989 | Kwak |
| 4,874,117 A | 10/1989 | Kay et al. |
| 4,879,781 A | 11/1989 | Desimone |
| 4,886,186 A | 12/1989 | Andris |
| 4,892,427 A | 1/1990 | Ford |
| D310,308 S | 9/1990 | Wolsey |
| 4,954,000 A | 9/1990 | Gueret |
| 4,957,125 A * | 9/1990 | Yaneza .................... 132/309 |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,066,155 A | 11/1991 | English et al. |
| 5,156,479 A | 10/1992 | Iizuka |
| 5,199,807 A | 4/1993 | Uchida |
| 5,234,136 A | 8/1993 | Kopis |
| 5,294,205 A | 3/1994 | Moeck et al. |
| 5,336,005 A | 8/1994 | Moeck et al. |
| 5,423,623 A | 6/1995 | Bakic |
| 5,540,361 A | 7/1996 | Fattori |
| 5,547,302 A | 8/1996 | Dornbusch et al. |
| 5,560,518 A | 10/1996 | Catterall et al. |
| 5,573,341 A | 11/1996 | Iaia |
| 5,697,531 A | 12/1997 | Fattori |
| 5,725,133 A | 3/1998 | Iaia |
| 5,765,573 A | 6/1998 | Gueret |
| 5,772,347 A | 6/1998 | Gueret |
| 5,803,640 A | 9/1998 | Nakajima et al. |
| 5,827,002 A | 10/1998 | Nakajima |
| 5,839,622 A | 11/1998 | Bicknell et al. |
| 5,851,079 A | 12/1998 | Horstman et al. |
| 5,860,572 A | 1/1999 | Harrold et al. |
| 5,879,095 A | 3/1999 | Gueret |
| 5,941,254 A | 8/1999 | Heler |
| 5,996,850 A | 12/1999 | Morali et al. |
| 6,015,293 A | 1/2000 | Rimkus |
| 6,071,026 A | 6/2000 | Martinez et al. |
| 6,082,918 A | 7/2000 | Gueret |
| 6,086,276 A | 7/2000 | Gueret |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |
| 6,368,001 B1 | 4/2002 | Roeder |
| 6,398,439 B1 | 6/2002 | Szekely |
| 6,406,694 B1 | 6/2002 | LaRosa |
| 6,450,716 B1 | 9/2002 | Szekely |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Lin |
| 6,745,781 B2 | 6/2004 | Gueret |
| 6,746,170 B2 | 6/2004 | Delage |
| 6,752,558 B1 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,244,073 B2 | 7/2007 | Trocino |
| 7,303,348 B2 | 12/2007 | Phipps et al. |
| 7,309,184 B2 | 12/2007 | Butcher et al. |
| 7,347,360 B2 | 3/2008 | Lasch et al. |
| 7,374,360 B1 | 5/2008 | Szekely |
| 7,396,180 B2 | 7/2008 | Bugla et al. |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,520,406 B2 | 4/2009 | Jaichandra et al. |
| 7,557,936 B2 | 7/2009 | Dickinson |
| 7,641,411 B2 | 1/2010 | Biegel |
| 7,651,291 B2 | 1/2010 | Py et al. |
| 7,665,923 B2 | 2/2010 | Py et al. |

(56) References Cited

U.S. PATENT DOCUMENTS

| | | |
|---|---|---|
| 2002/0054783 A1 | 5/2002 | Gueret |
| 2002/0073496 A1 | 6/2002 | Kim |
| 2003/0057236 A1 | 3/2003 | Delage |
| 2004/0028456 A1 | 2/2004 | Giraldo |
| 2005/0006409 A1 | 1/2005 | Ganzeboom |
| 2005/0026774 A1 | 2/2005 | Nolan |
| 2006/0207627 A1 | 9/2006 | Thorpe et al. |
| 2006/0233588 A1 | 10/2006 | Gueret |
| 2006/0269354 A1 | 11/2006 | Lane |
| 2006/0275225 A1 | 12/2006 | Prencipe et al. |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0189888 A1 | 8/2008 | Hohlbein |
| 2008/0274066 A1 | 11/2008 | Montgomery |
| 2009/0074679 A1 | 3/2009 | Silverman |
| 2009/0261007 A1 | 10/2009 | Sanchez |
| 2009/0317432 A1 | 12/2009 | Kergosien |

FOREIGN PATENT DOCUMENTS

| | | |
|---|---|---|
| FR | 907669 | 3/1946 |
| FR | 1596074 | 6/1970 |
| FR | 2597734 | 10/1987 |
| GB | 666082 | 2/1952 |
| GB | 2085717 | 5/1982 |
| GB | 2280361 | 2/1995 |
| JP | 48-093167 | 12/1973 |
| RU | 44471 | 3/2005 |
| WO | WO 2004/112637 | 12/2004 |
| WO | WO 2008/062935 | 5/2008 |
| WO | WO 2009/151455 | 12/2009 |

OTHER PUBLICATIONS

International Search Report and Written Opinion in International Application No. PCT/US09/069408 mailed Jul. 23, 2010.
International Search Report and Written Opinion in International Application No. PCT/US09/069402 mailed Jul. 23, 2010.
International Search Report and Written Opinion in International Application No. PCT/US10/060861 mailed Jun. 8, 2011.
International Search Report and Written Opinion in International Application No. PCT/US10/049102 mailed Jun. 7, 2011.

* cited by examiner

ORAL CARE SYSTEM, KIT AND METHOD

CROSS-REFERENCE TO RELATED APPLICATIONS

This application is a national stage application of PCT/US2010/060874, filed Dec. 22, 2010, which is a continuation in part of International Application No. PCT/US2009/069408 filed on Dec. 23, 2009 and International Application No. PCT/US2009/069402 filed on Dec. 23, 2009. PCT/US2010/060874 also claims priority to U.S. Provisional Application No. 61/410,514 filed on Nov. 5, 2010; U.S. Provisional Application No. 61/423,397 filed on Dec. 15, 2010; U.S. Provisional Application No. 61/423,414 filed on Dec. 15, 2010; U.S. Provisional Application No. 61/423,435 filed on Dec. 15, 2010; and U.S. Provisional Application No. 61/423,449 filed on Dec. 15, 2010, all of which are incorporated herein by reference.

FIELD OF THE INVENTION

The present invention relates generally to oral care systems, kits and methods, and specifically to a system, kit and method including a toothbrush having an open cavity that retains a removable dispenser containing a fluid.

BACKGROUND OF THE INVENTION

Oral care products or agents are applied in different ways. For example, without limitation, a common technique used for tooth whitening products is to cast an impression of a person's teeth and provide a tray of the shape of this impression. A person then only needs to add a whitening composition to the tray and to apply the tray to his/her teeth. This is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to one's teeth. After a few treatments the teeth gradually whiten.

A problem with existing brushing techniques is that saliva in the mouth contains the enzyme catalase. This enzyme will catalize the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

Further difficulties arise in that dispensers used for dispensing fluid materials have a tendency to weep after use due to pressure exerted on the fluid in the reservoir from the elevator.

A more portable, compact and convenient way to store oral care products, and to dispense and apply those oral care products to oral surfaces is desired.

BRIEF SUMMARY OF THE INVENTION

Embodiments of the present invention provide an efficient, compact, and portable oral care system that combines an oral care implement such as a toothbrush with a fluid dispenser in a highly portable and convenient housing. Advantageously, such embodiments are especially suited for easy transport and/or travel.

Exemplary embodiments of the present invention are directed to a toothbrush that detachably retains a removable dispenser containing a fluid reservoir. In some exemplary embodiments, the oral care system includes fluid such as fluidic oral care materials, either active or non-active agents, that may include without limitation, whitening, enamel protection, anti-sensitivity, fluoride, tartar protection, or other oral care materials. The dispenser can be detachably docked and stored at least partially within the handle of the toothbrush so that a portion of the dispenser protrudes from the toothbrush, or forms a proximal end of the toothbrush handle, to permit access to a user for easy removal and use of the dispenser. The dispenser can be completely removable from the toothbrush in certain embodiments so that the user can apply the fluid to his/her teeth with ease, and then reinsert the dispenser in the toothbrush for convenient storage. In certain embodiments, the dispenser may be a pen-like component. The toothbrush can removably and non-fixedly secure the dispenser within the handle so that the dispenser can be repetitively removed and reinserted therein. In some embodiments, the dispenser may be adapted to be user-refillable for repeated use.

In one embodiment, the invention can be an oral care system comprising: a toothbrush; and a dispenser detachably coupled to the toothbrush, the dispenser comprising: a housing having a longitudinal axis and an internal reservoir for containing a fluid; a dispensing orifice in the housing for dispensing the fluid from the reservoir; a collar within the housing, the collar comprising an axial passageway and a cam surface, the collar being non-rotatable with respect to the housing; a reciprocator comprising an actuator, a drive screw extending through the axial passageway of the collar, and a cam surface, the reciprocator being rotatable with respect to the housing; a resilient member that axially biases the cam surface of the reciprocator and the cam surface of the collar into mating contact; an elevator forming an end wall of the reservoir, the elevator being non-rotatable with respect to the housing and threadily coupled to the drive screw; and wherein rotation of the actuator causes the elevator to (1) axially advance along the drive screw in a first axial direction due to relative rotation between the drive screw and the elevator, and (2) axially reciprocate due to relative rotation between the cam surface of the collar and the cam surface of the reciprocator.

In another embodiment, the invention can be an oral care system comprising: a toothbrush; and a dispenser detachably coupled to the toothbrush, the dispenser comprising: a housing forming an internal cavity extending along a longitudinal axis; an elevator disposed within the internal cavity that hermetically separates the internal cavity into a reservoir for containing a fluid and a chamber, the elevator comprising an outer surface forming an end wall of the reservoir and an inner surface forming an end wall of the chamber, the elevator being non-rotatable with respect to the housing; a dispensing orifice in the housing for dispensing the fluid from the reservoir; an actuator; a drive screw in the chamber and operably coupled to the actuator, the drive screw and the actuator being rotatable with respect to the housing, wherein the drive screw does not penetrate through the outer surface of the elevator into the reservoir; and an extension member having a first end coupled to the elevator and a second end threadily coupled to the drive screw, the extension member being non-rotatable with respect to the housing; and wherein rotation of the actuator causes the elevator to axially advance along the drive screw in a first axial direction due to relative rotation between the drive screw and the extension member.

In yet another embodiment, the invention can be an oral care system comprising: a toothbrush; and a dispenser detachably coupled to the toothbrush, the dispenser comprising: a housing having a longitudinal axis and an internal reservoir for containing a fluid; a dispensing orifice in the housing for dispensing the fluid from the reservoir; a first cam surface within the housing, the first cam surface being non-rotatable with respect to the housing; a reciprocator comprising an actuator, a drive screw, and a second cam surface, the reciprocator being rotatable with respect to the housing; a resilient member that axially biases the second cam surface and the cam surface of the collar into mating contact, wherein the mating contact between the first cam surface and the second cam surface prevents the reciprocator from being uncoupled from the housing; an elevator forming an end wall of the reservoir, the elevator being non-rotatable with respect to the housing and threadily coupled to the drive screw; wherein rotation of the actuator causes the elevator to (1) axially advance along the drive screw in a first axial direction due to relative rotation between the drive screw and the elevator, and (2) axially reciprocate due to relative rotation between the first cam surface and the second cam surface.

In still another embodiment, the invention can be an oral care system comprising: a toothbrush; and a dispenser detachably coupled to the toothbrush, the dispenser comprising: a housing forming an internal cavity extending along a longitudinal axis; an elevator disposed within the internal cavity that hermetically separates the internal cavity into a reservoir for containing a fluid and a chamber, the elevator comprising an outer surface forming an end wall of the reservoir and an inner surface forming an end wall of the chamber, the elevator being non-rotatable with respect to the housing; a dispensing orifice in the housing for dispensing the fluid from the reservoir; an actuator; a drive screw in the chamber and operably coupled to the actuator, the drive screw and the actuator being rotatable with respect to the housing, wherein the drive screw does not penetrate through the outer surface of the elevator into the reservoir when the elevator is in a fully retracted position; and the elevator operbaly coupled to the drive screw so that rotation of the actuator causes the elevator to axially advance along the drive screw in a first axial direction due to relative rotation between the drive screw and the elevator.

In certain exemplary embodiments, any suitable fluid may be used with embodiments and methods described herein according to the present invention. Accordingly, the oral care treatment system may be any type of system including without limitation tooth whitening, enamel protection, anti-sensitivity, fluoride, tartar protection/control, and others. The invention is expressly not limited to any particular type of oral care system or oral care material, unless specifically claimed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplified embodiments will be described with reference to the following drawings in which like elements are labeled similarly.

The present invention will become more fully understood from the detailed description and the accompanying drawings, wherein.

DETAILED DESCRIPTION OF THE INVENTION

Figure 1:
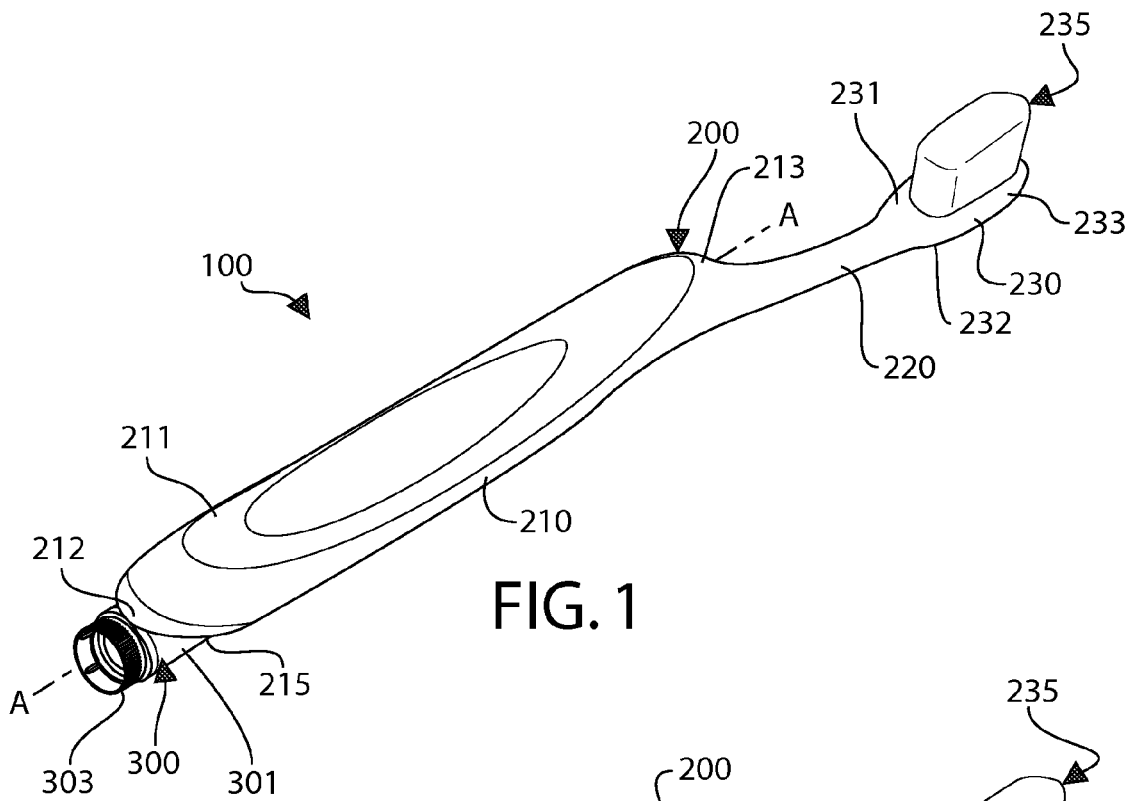
FIG. 1 is a front perspective view of an oral care system including a toothbrush and a fluid dispenser according to one embodiment of the present invention, wherein the dispenser is coupled to the toothbrush.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

In the description of embodiments of the invention disclosed herein, any reference to direction or orientation is merely intended for convenience of description and is not intended in any way to limit the scope of the present invention. Moreover, the features and benefits of the invention are illustrated by reference to exemplified embodiments. Accordingly, the invention expressly should not be limited to such exemplified embodiments illustrating some possible but non-limiting combination of features that may be provided alone or in other combinations of features; the scope of the invention being defined by the claims appended hereto.

Exemplary embodiments of the present invention will now be described with respect to one possible oral care or treatment system. Embodiments of the oral care system may include without limitation the following fluids such as fluidic oral care materials including: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of fluid and the invention is expressly not limited to any particular oral care system or fluidic oral care material alone.

Figure 2:
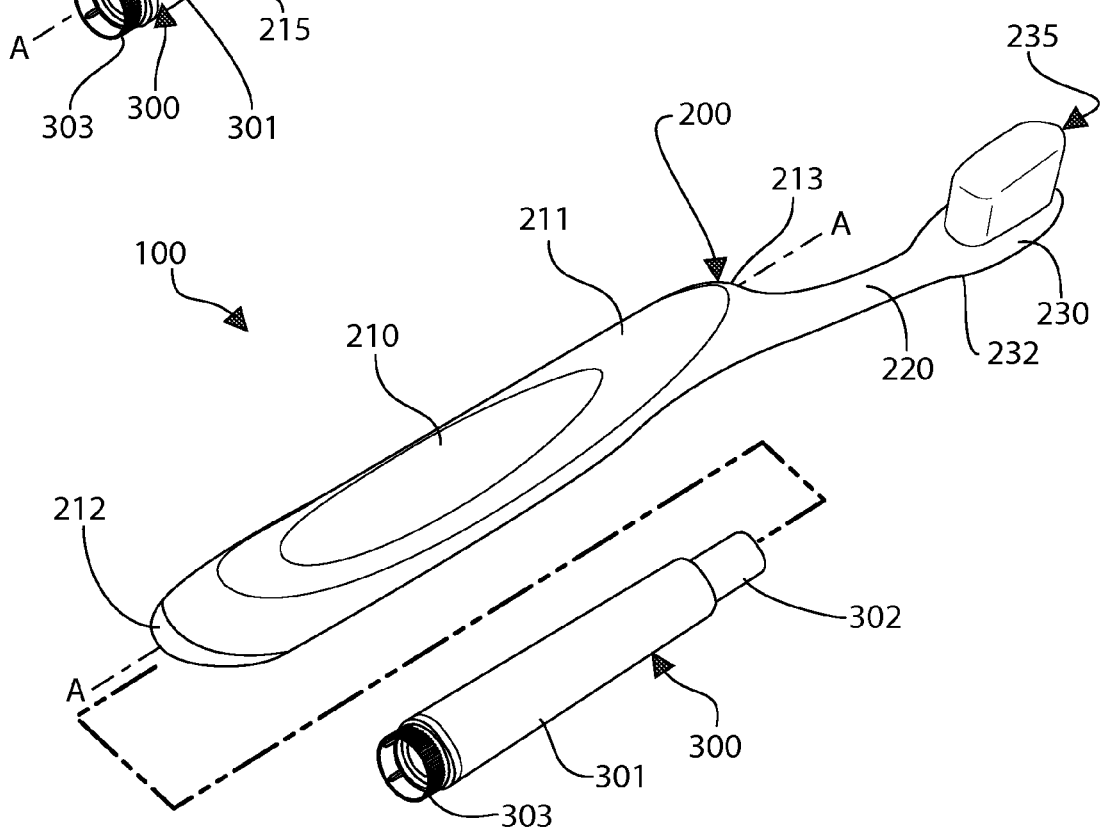
FIG. 2 is a front perspective view of the oral care system of FIG. 1 wherein the fluid dispenser is removed from the toothbrush.

Referring to FIGS. 1-2, an oral care system 100 is illustrated according to one embodiment of the present invention. The oral care system 100 is a compact readily portable self-contained user-friendly system that comprises all of the necessary components and chemistries necessary for a user to perform a desired oral care treatment routine. As will be described in greater detail below, the oral care system 100 in one exemplary embodiment generally takes the form of a modified toothbrush having a removable dispenser 300 disposed at least partially within its handle. Because the dispenser 300 is located within the handle of the toothbrush itself, the oral care system 100 is portable for travel, easy to use, and reduces the amount of required storage space. Furthermore, since the toothbrush 200 and dispenser 300 are housed together, the user is less likely to misplace the dispenser 300 and be more inclined to maintain the oral treatment routine with the dispenser 300 since brushing will remind the user to simply detach and apply the contents of the dispenser 300.

The oral care system 100 generally comprises a toothbrush body 200 (hereinafter referred to simply as a toothbrush) and a dispenser 300. While the invention is described herein with respect to the use of a toothbrush as one of the two primary components of the oral care system 100, it is to be understood that other alternate oral care implements can be used within the scope of the invention, including tongue cleaners, tooth polishers and specially designed ansate implements having tooth engaging elements. In certain instances, the toothbrush 200 may include tooth engaging elements that are specifically designed to increase the effect of the active agent in the dispenser on the teeth. For example, the tooth engaging elements may include elastomeric wiping elements that assist in removing stains from teeth and/or assist with forcing the oral care agent into the tubules of the teeth. Moreover, while the toothbrush 200 is exemplified as a manual toothbrush, the toothbrush may be a powered toothbrush in other embodiments of the invention. It is to be understood that the inventive system can be utilized for a variety of intended oral care needs by filling the dispenser 300 with any fluid, such as a fluidic oral care material including an oral care agent that achieves a desired oral effect. In one embodiment, the fluid, is free of (i.e., is not) toothpaste as the dispenser 300 is intended to augment not supplant the brushing regimen. The fluid can be selected to complement a toothpaste formula, such as by coordinating flavors, colors, aesthetics, or active ingredients.

The toothbrush 200 generally comprises a handle portion 210, a neck portion 220 and a head portion 230. The handle 210 provides the user with a mechanism by which he/she can readily grip and manipulate the toothbrush 200. The handle 210 may be formed of many different shapes, sizes, materials and a variety of manufacturing methods that are well-known to those skilled in the art, so long as it can house the dispenser 300 therein as described in detail below. If desired, the handle 210 may include a suitable textured grip 211 made of soft elastomeric material. The handle 210 can be a single or multi-part construction. The handle 210 extends from a proximal end 212 to a distal end 213 along a longitudinal axis A-A. A cavity (not visible) is formed within the handle 210. An opening 215 is provided at the proximal end 212 of the handle 210 that provides a passageway into the cavity through which the dispenser 300 can be inserted and retracted. While the opening 215 is located at the proximal end 212 of the handle in the exemplified embodiment, the opening 215 may be located at other positions on the handle 210 in other embodiments of the invention. For example, the opening 215 may be located on a longitudinal surface of the handle 210 (e.g., the front surface, the rear surface and/or the side surfaces) and be elongated to provide sufficient access to the cavity.

The handle 210 transitions into the neck 220 at the distal end 213. While the neck 220 generally has a smaller transverse cross-sectional area than the handle 220, the invention is not so limited. Broadly speaking, the neck 220 is merely the transition region between the handle 210 and the head 230 and can conceptually be considered as a portion of the handle 210. In this manner, the head 230 is connected to the distal end 213 of the handle 210 (via the neck 220).

The head 230 and the handle 210 of the toothbrush 200 are formed as a single unitary structure using a molding, milling, machining or other suitable process. However, in other embodiments, the handle 210 and head 230 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 230 and handle 210 are of a unitary or multi-piece construction (including connection techniques) is not limiting of the present invention, unless specifically stated. In some embodiment of the invention, the head 230 may be detachable (and replaceable) from the handle 210 using techniques known in the art.

The head 230 generally comprises a front surface 231, a rear surface 232 and a peripheral side surface 233 that extends between the front and rear surfaces 231, 232. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 of the head 230 comprises a collection of oral cleaning elements such as tooth engaging elements 235 extending therefrom for cleaning and/or polishing contact with an oral surface and/or interdental spaces. While the collection of tooth engaging elements 235 is suited for brushing teeth, the collection of cleaning elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 230 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed to be non-fixedly secured together when in an assembled state (referred to herein as a storage state) and completely isolated and separated from one another when in a disassembled state (referred to herein as an application state). The toothbrush 200 and the dispenser 300 are illustrated in the storage state in FIG. 1 and in the application state in FIG. 2. The dispenser 300 can be slidably manipulated and moved between the storage state (FIG. 1) in which the dispenser 300 is docked in the toothbrush handle portion 210 and the application state (FIG. 2) in which the dispenser 300 is removed from the handle portion 210 by the user as desired. The dispenser 300 will now be described in greater detail.

Figure 3:
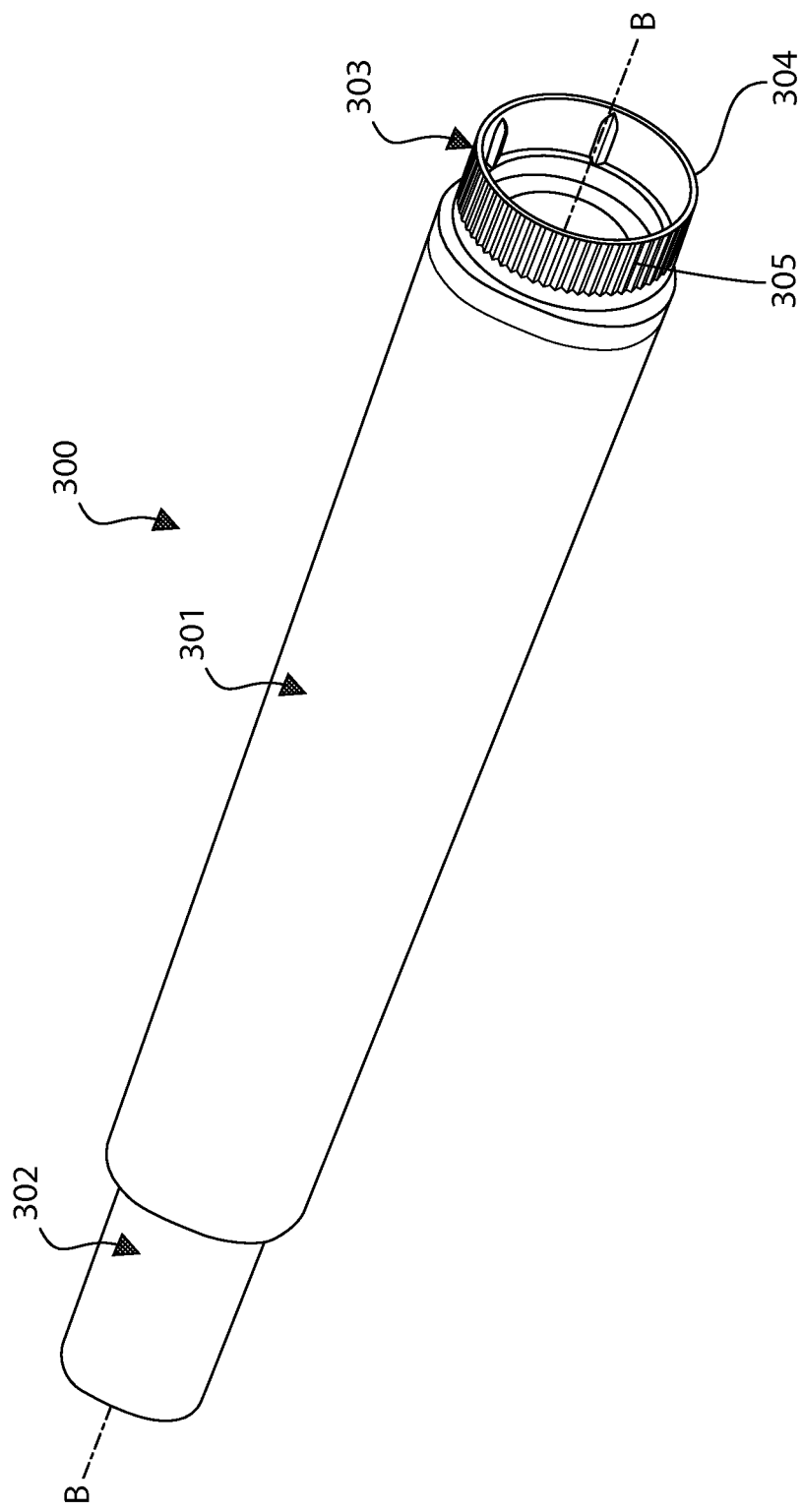
FIG. 3 is a perspective view of the fluid dispenser of the oral care system of FIG. 1.
Figure 5:
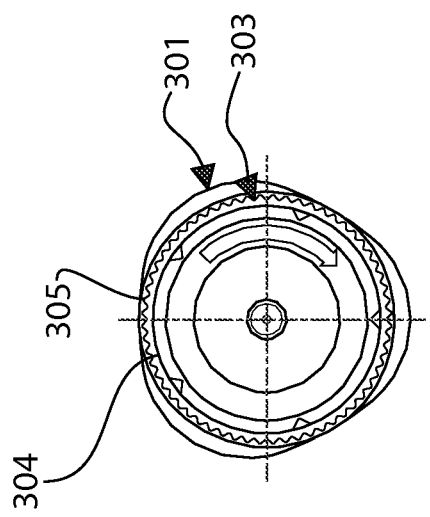
FIG. 5 is a bottom view of the fluid dispenser of FIG. 3.
Figure 4:
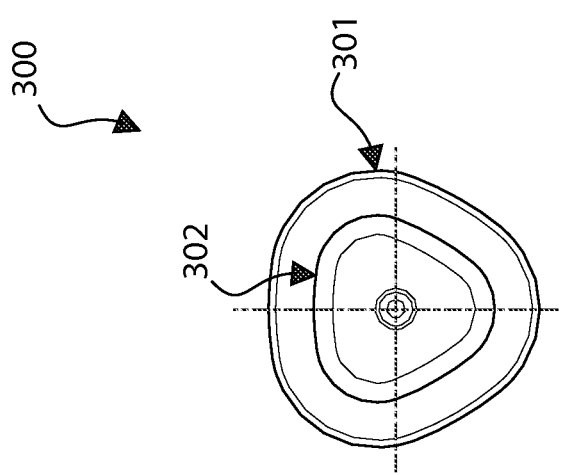
FIG. 4 is a top view of the fluid dispenser of FIG. 3.

Referring now to FIGS. 3-5 concurrently, the dispenser 300 is schematically illustrated. The dispenser 300 is an elongated tubular pen-like structure that extends along longitudinal axis B-B. The dispenser 300 generally comprises a housing 301, a removable cap 302 coupled to one end of the housing 301, and an actuator 303 extending from an opposite end of the housing 301. The dispenser 300 is designed so as to be capable of being operated to dispense the fluid stored therein using a single hand. Specifically, the dispenser is positioned in a user's hand so that the actuator 303 is lodged in the palm of the user's hand. The user then uses the fingers of that same hand to rotate the housing 301 (while keeping the actuator 303 stationary relative to the housing 301). As a result, the fluid container therein is dispensed from the dispenser 300. The dispensing mechanism will be described in greater detail below.

The housing 301 has a non-circular transverse cross-sectional profile (shown in FIGS. 4-5). In the exemplified embodiment, the housing 301 has a generally triangular transverse cross-sectional profile having rounded corners. Of course, in other embodiments, the housing 301 can take on other non-circular shapes, or can be circular in certain alternative embodiments. For example, in the embodiment exemplified in FIGS. 17-19B, the housing 301C of the dispenser 300C has a generally circular transverse cross-sectional profile. However, by forming the housing 301 to have a non-circular transverse cross-sectional profile, rotation of the dispenser 300 when it is in the storage state within the handle portion 210 of the toothbrush 200 is prevented.

The actuator 303 protrudes axially from the housing 301 so that a user can easily grip and rotate the actuator 303. A plurality of protuberances 305, in the form of axial aligned and space-apart ridges, are formed on the outer surface 304 of the actuator 303 to further facilitate gripping and rotation. As discussed in greater detail below, the actuator 303 is part of a larger reciprocator component that is coupled to the housing 301. However, in other embodiments, such as the one exemplified in FIGS. 17-19, the actuator 303C may be formed as a separate component that is non-rotatably coupled to the reciprocator 306C. As is also discussed in greater detail below, the actuator 303 is rotatable with respect to the housing 301 and axially reciprocates along axis B-B during rotation. In the exemplified embodiment, the actuator 303 has a wheel having a substantially circular transverse cross-sectional profile. As can be seen in FIG. 5, the actuator 303 is sized and shaped so that its transverse cross-sectional profile fits within the transverse cross-sectional profile of the housing 301.

The cap 302 has a transverse cross-sectional profile that corresponds in shape to the transverse cross-sectional profile of the housing 301, and is also non-circular to facilitate gripping and/or twisting to remove the cap from the housing so that the fluidcan be dispensed from the internal reservoir of the dispenser 300.

Figure 6:
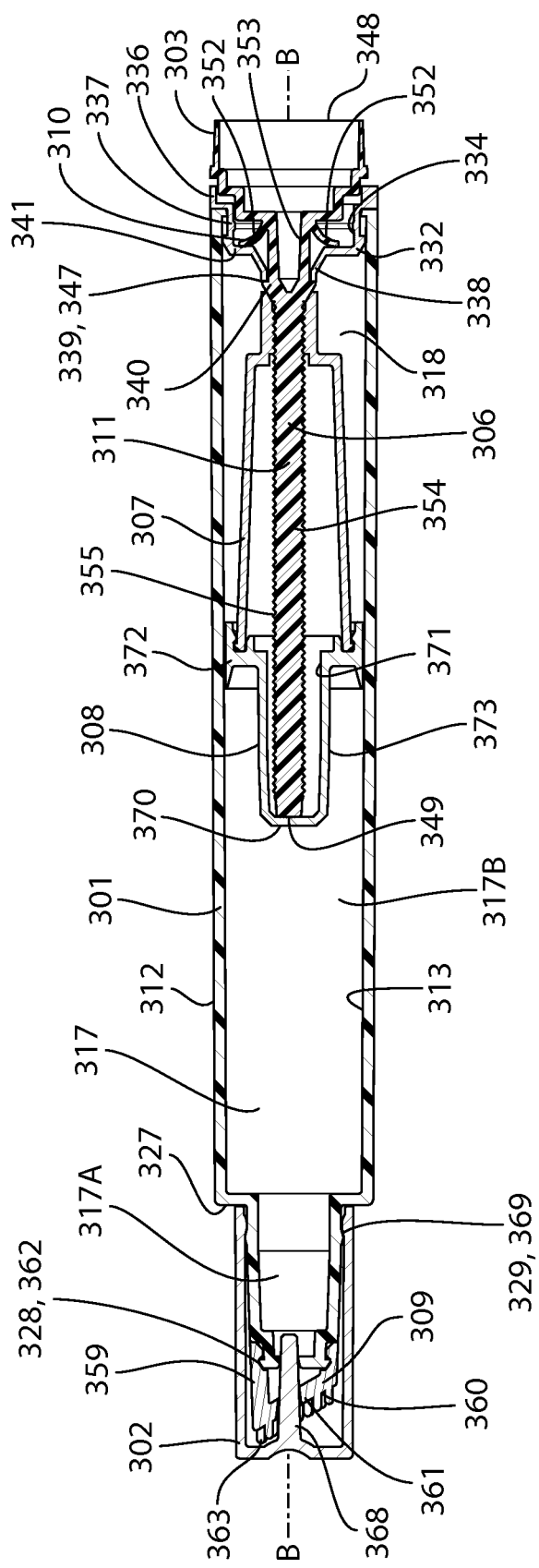
FIG. 6 is a longitudinal cross-sectional view of the dispenser of FIG. 3.

Referring now to FIG. 6, the components of the dispenser 300 will be described in greater detail. The dispenser 300 generally comprises a housing 301, a cap 302, a reciprocator 306, an extension member 307, an elevator 308, a collar 332 and an applicator 309. The reciprocator 306 comprises the actuator 303, a resilient member 310 and a drive screw 311. In the exemplified embodiment, the actuator 303, the resilient member 310 and the drive screw 311 are integrally formed to form the reciprocator 306 as a unitary structure. However, in certain embodiments, the actuator 303, the resilient member 310 and the drive screw 311 may be formed as separate components that are subsequently coupled together and/or properly positioned within the dispenser 300 in a cooperative manner as described below. Furthermore, in certain embodiments, the resilient member 310 can conceptually and/or physically be a separate component from the reciprocator 306.

Figure 9:
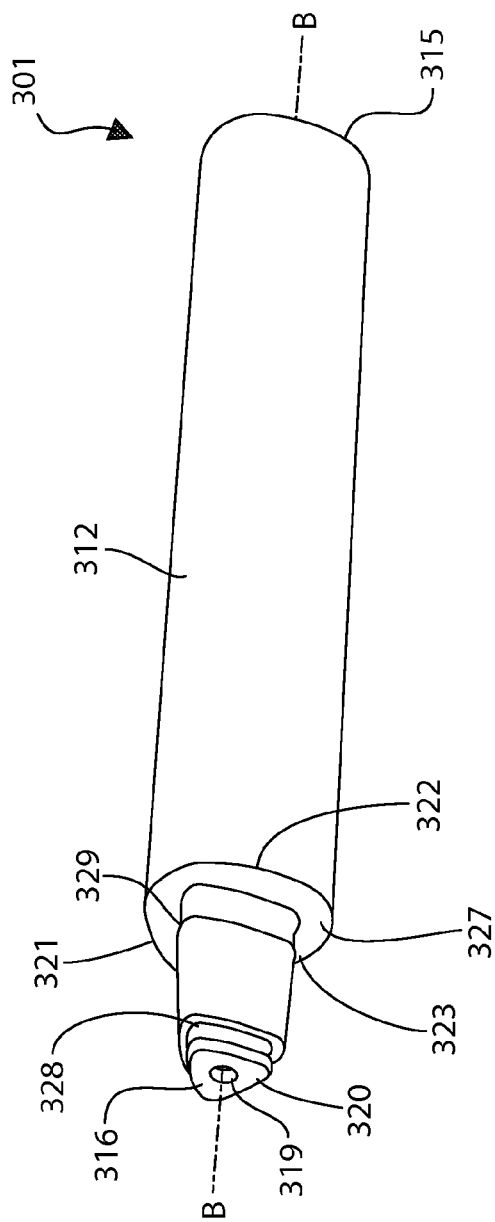
FIG. 9 is a perspective view of the housing of the fluid dispenser of FIG. 3.
Figure 10:
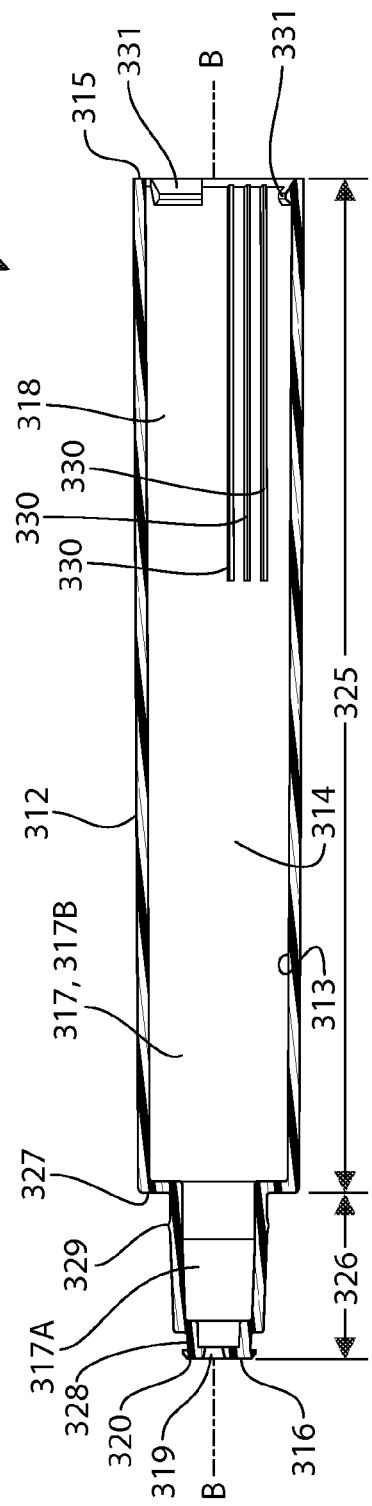
FIG. 10 is a longitudinal cross-sectional view of the housing of the fluid dispenser of FIG. 3.

Referring now to FIGS. 6 and 9-10 concurrently, the housing 301 will be described in greater detail. The housing 301 is constructed of a material that is sufficiently rigid to provide the necessary structural integrity for the dispenser 300. For example, the housing 301 can be formed of a moldable hard plastic. Suitable hard plastics include polymers and copolymers of ethylene, propylene, butadiene, vinyl compounds and polyesters such as polyethylene terephthalate. The chosen plastic(s), however, should be compatible with the oral care material that is to be stored within the dispenser 300 and should not be corroded or degraded by the oral care fluid.

While the housing 301 is exemplified as a single layer construction, in certain embodiments, the housing may be a multilayer construction. In certain multi-layer embodiments, an inner layer can be formed from the hard plastic materials described immediately above while an outer layer can be formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness. While an over-molding construction is one suitable method of forming the outer layer, a suitable deformable thermoplastic material, such as TPE, may be formed in a thin layer and attached to inner layer with an appropriate adhesive, sonic welding, or by other means.

The housing 301 is an elongated hollow tubular structure extending along the longitudinal axis B-B from a proximal end 315 to a distal end 316. As discussed above, the housing 301 has a non-circular transverse cross-sectional profile. In the exemplified embodiment, the housing 301 is formed by three longitudinal side walls 321-323, thereby giving the housing a tri-lobe transverse cross-sectional profile. Of course, the invention is not so limited and the housing 301 can take on a wide variety of transverse cross-sectional profiles, whether circular or non-circular as desired.

The housing 301 comprises an outer surface 312 and an inner surface 313 that forms an elongated internal cavity 314.

As discussed in greater detail below, when the dispenser 300 is fully assembled, the internal cavity 314 of the housing 301 is divided into a reservoir 317 and a chamber 318 by the elevator 308. A dispensing orifice 319 is provided in the distal end 316 of the housing 301 through which fluid stored in the reservoir 317 is dispensed from the dispenser 300. In the exemplified embodiment, the dispensing orifice 319 is located in a transverse end wall 320 as the distal end 316 of the housing 301. The dispensing orifice 319 is positioned in the transverse end wall 320 so that a center-point of the dispensing orifice 319 is coincident with the longitudinal axis B-B. Moreover, in certain other embodiment, the dispensing orifice 319 can be located in other areas of the housing 301, such as on one of the longitudinal side walls 321-323.

The housing 301 comprises a first longitudinal section 325 and a second longitudinal section 326. The second longitudinal section 326 has a reduced transverse cross-section in comparison to the first longitudinal section 325. The second longitudinal section 326 extends axially from an annular transverse shoulder 327 of the housing 301. The reservoir 317 occupies both a distal section of the first longitudinal section 325 and the second longitudinal section 326. The chamber 318, on the other hand, occupies only a proximal section of the first longitudinal section 325. As a result of the reservoir 317 occupying both a distal section of the first longitudinal section 325 and the second longitudinal section 326, the reservoir 317 comprises a section 317A located within the second longitudinal section 326 that has a reduced transverse cross-section in comparison to the section 317B of the reservoir 317 located within the distal section of the first longitudinal section 325.

The second longitudinal section 326 of the housing 301 comprises a depression 328 near the distal end 316 for facilitating coupling of the applicator 309 to the housing 301. In the exemplified embodiment, the depression 328 is in the form of annular groove. Of course, the depression 328 can take on wide variety of embodiments, including dimples, notches, etc. A protuberance 329 is also provided on the second longitudinal section 326 of the housing 301 for facilitating coupling of the removable cap 302 to the housing 301. In the exemplified embodiment, the protuberance 329 is in the form of an annular ridge. Of course, the protuberance 329 can take on wide variety of embodiments, including tangs, prongs, bumps, ridges, etc. The protuberance 329 is located on the second longitudinal section 326 at a location closer to the shoulder 327 than the annular groove 328.

A plurality of circumferentially spaced-apart grooves 330 are formed in the inner surface 313 of the housing 301. The grooves 330 are located within the chamber 318 of the internal cavity 314 and extend axially from the proximal end 315. The grooves 330 are provided to receive corresponding ridges and/or protuberances provided on the outer surface of the collar 332 to prevent relative rotation between the collar 332 and the housing 301 when the collar 332 is assembled to the housing 301. The mating between the ridges/protuberances of the collar 332 and the grooves 330 of the housing 301 can be important in embodiments of the dispenser 300 in which the internal cavity 314 has a circular transverse cross-sectional shape. However, in embodiments where the internal cavity 314 has a non-circular shape, relative rotation between the housing 301 and the collar 332 is prevented due simply to the nin-circular transverse cross-sectional geometry.

A plurality of flanges 331 are provided on the inner surface 313 of the housing 301 that extend radially inward toward the longitudinal axis B-B. The flanges 331 are located at the proximal end 315 of the housing 301 and are arranged in a circumferentially spaced-apart manner. In certain embodiments, a single continuous annular flange, or other protuberant structures, can be provided instead of the plurality of flanges 331. The flanges 331 help retain the collar 332 in coupling with the housing 301 after the dispenser 300 is assembled, thereby assisting in preventing the collar 332 from being separated from the housing 301 due to an axially applied force and/or movement.

Figure 15:
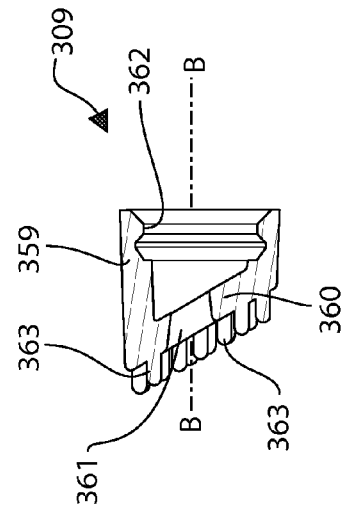
FIG. 15 is a longitudinal cross-sectional view of the applicator of the fluid dispenser of FIG. 3.
Figure 14:
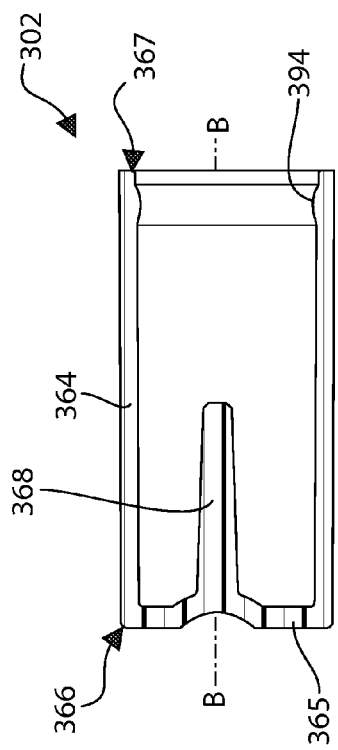
FIG. 14 is a longitudinal cross-sectional view of the cap of the fluid dispenser of FIG. 3.

Referring now to FIGS. 6 and 14-15, the details of the applicator 309 and the removable cap 302 will be described, along with their structural cooperation with the housing 301. The applicator 309, in the exemplified embodiment, is formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitbale range of the hardness durometer rating is between A25 to A40 Shore hardness.

In alternative embodiments, the applicator 309 may be constructed of bristles, a porous or sponge material, or a fibrillated material. Suitable bristles include any common bristle material such as nylon or PBT. The sponge-like materials can be of any common foam material such as urethane foams. The fibrillated surfaces can be comprised of various thermoplastics. The invention, however, is not so limited and the applicator 309 can be any type of surface and/or configuration that can apply a viscous substance onto the hard surface of teeth, including merely an uncovered opening/orifice.

The exemplary applicator 309 comprises a tubular sidewall 359 and a transverse end wall 360. An aperture 361 is provided in the end wall 360 through which fluid from the reservoir 317 can be dispensed. A protuberance 362, in the form of an annular ridge, is formed on an inner surface of the sidewall 359. A plurality of protuberances 363, in the form of nubs, extend from the outer surface of the end wall 360.

When the applicator 309 is coupled to the second longitudinal section 326 of the housing 301, the protuberance 362 of the applicator 309 nests within the depression 328 of the housing 301. Furthermore, the aperture 361 of the applicator 309 is aligned with the dispensing orifice 319 of the housing 301.

Similar to the housing, the applicator 309 has a non-circular transverse cross-sectional profile in the exemplary embodiment. More specifically, the applicator 309 has a tri-lobe transverse cross-sectional profile. Of course, the invention is not so limited and the housing can take on a wide variety of transverse cross-sectional profiles, whether circular or non-circular as desired.

The removable cap 302 comprises a tubular sidewall 364 and a transverse end wall 365. The removable cap 302 has a closed top end 366 and open bottom end 367. An axial plug 368 extends axially from a bottom surface of the end wall 365. A protuberance 394, in the form of an annular ridge, protrudes from an inner surface of the sidewall 364. The removable cap 302 couples to the housing 301 by being slid over the second longitudinal section 326 of the housing 301. Mating between the protuberance 394 of the removable cap 302 and the protuberance 329 of the housing 301 secures the removable cap 302 to the housing 301. The axial plug 368 extends into through and seals the aperture 361 of the applicator 309 and the dispensing orifice 319 of the housing 301, thereby preventing leaking and/or drying out of the fluid in the reservoir 317.

Figure 11:
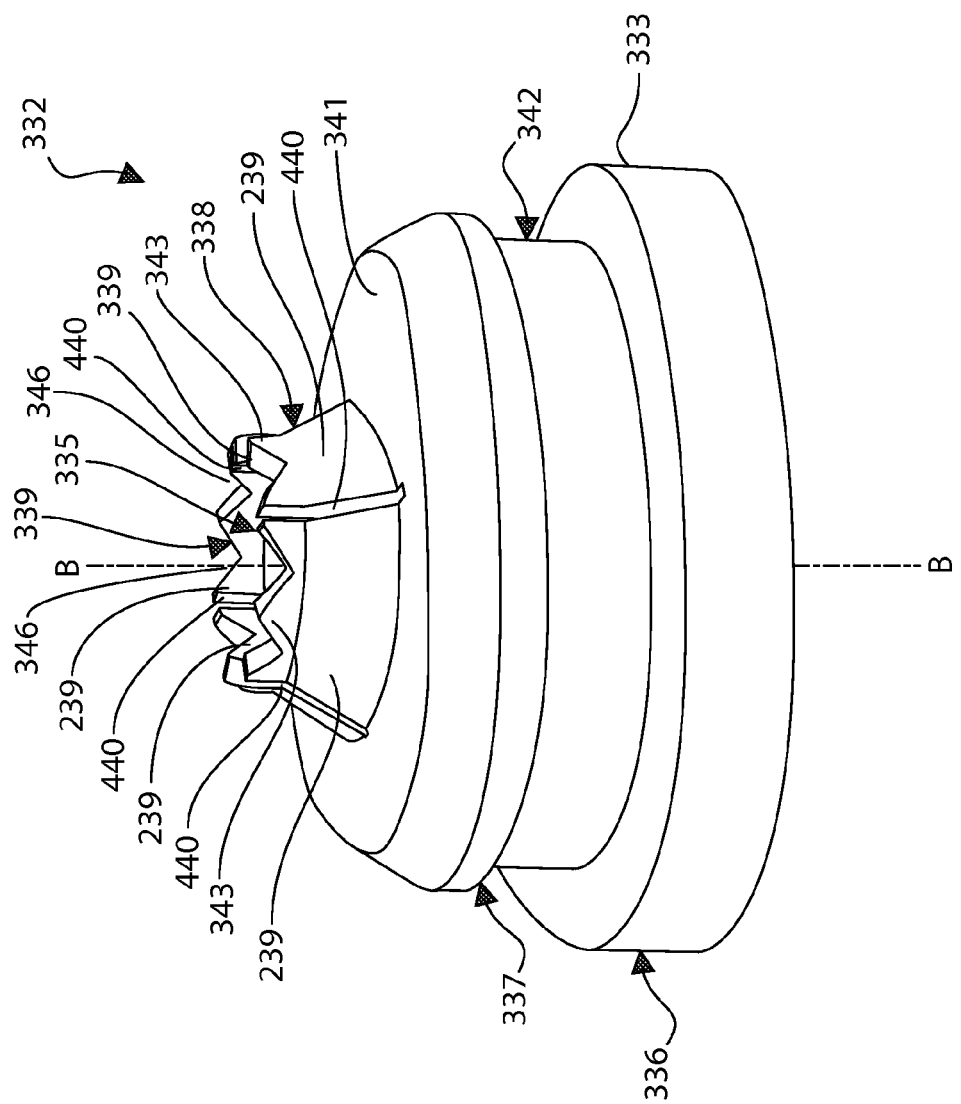
FIG. 11 is a perspective view of the collar of the fluid dispenser of FIG. 3.

Referring now to FIGS. 6 and 11 concurrently, the collar 332 will be described in greater detail. The collar 332 is constructed of a material that is sufficiently rigid to provide the necessary structural integrity to perform the functions discussed below. In one embodiment, the collar 332 can be formed of a moldable hard plastic. Suitable hard plastics include polymers and copolymers of ethylene, propylene, butadiene, vinyl compounds and polyesters such as polyethylene terephthalate.

In the exemplified embodiment, the collar 332 is an annular ring-like structure comprising an outer surface 333 and an inner surface 334. The inner surface 334 forms an axial passageway 335 that extends through the entirety of the collar 332. The axial passageway 335 extends along the longitudinal axis B-B so that the drive screw 311 of the reciprocator 306 can be extended therethrough. The collar 332 comprises a flange portion 336, a plug portion 337 and a neck portion 338. The neck portion 338 extends from a shoulder 341 of the collar 332 disposed between the neck portion 338 and the plug portion 337. A depression 342, in the form of an annular groove, is provided in the outer surface 333 of the plug portion 337 of the collar 332.

When the dispenser 300 is assembled, the collar 332 is coupled to the housing 301 as illustrated in FIG. 6. When the dispenser 300 is assembled, the plug portion 337 and the neck portion 338 of the collar 332 are disposed within the internal cavity 314 (specifically chamber 318) of the housing 301. The flange portion 336 abuts the proximal end 315 of the housing 301, thereby preventing over-insertion of the collar 332 into the internal cavity 314. The flanges 331 of the housing 301 project into the depression 342 of the plug portion 337, thereby mating together to prevent the collar 332 from being withdrawn axially from the housing 301. The coupling of the collar 332 to the housing 301 is further effectuated by assuring that the tolerances are selected so that an additional interference fit is effectuated between the outer surface 333 of the collar 332 and the inner surface 313 of the housing. When coupled to the housing 301, the collar 332 is non-rotatable with respect to the housing 301. Of course, other cooperative structures and connection techniques can be used to couple the collar 332 to the housing 301 so that relative rotation between the two is prohibited.

In the exemplified embodiment, the neck portion 338 is formed by a plurality of arcuate segments 239 that protrude axially from the plug portion 337 and circumferentially surround the axial passageway 335 (and the drive screw 311 when the dispenser 300 is assembled). Adjacent arcuate segments 239 are separated by a gap 440. The neck portion 338 is formed by segments 239 to provide radial flexibility to the neck portion 338 so that a base portion 340 of the drive screw 311 can pass through the neck portion 338 during assembly. During assembly, as the base portion 340 of the drive screw 311 passes through the neck portion 338, the segments 239 flex radially outward, thereby allowing the base portion 340 to pass therethrough. However, once the base portion 340 of the drive screw 311 has fully passed through the neck portion 338, the segments 239 snap radially inward, returning to their initial position and preventing the reciprocator 306 from being separated from the collar 332. In other embodiments, the neck portion 338 can be constructed as a continuous structure rather than a plurality of segments 239 if desired.

The neck portion 338 of the collar 332 further comprises an upper cam surface 339 comprising a plurality of axially extending cams 343. In the exemplified embodiment, the cams 343 are saw-toothed protuberances having inclined surfaces 344 that terminate at an apex 345 (FIG. 16B). Of course, the cams 343 can take on a variety different shapes, such as contoured, etc. The upper cam surface 339 is an undulating transverse surface in the exemplified embodiment. A depression/notch 346 is located between adjacent cams 343. As discussed in greater detail below, the upper cam surface 339, in conjunction with the lower cam surface 347 of the reciprocator 306, causes the elevator 308 to axially reciprocate when relative rotational motion is created between the cam surfaces 339, 347.

While the collar 332 is a separate component than the housing 301 in the exemplified embodiment of the dispenser 300, in other embodiment the collar 332 can be integrally formed as a part of the housing 301. In such an embodiment, the housing 301 itself would comprise the upper cam surface 339.

Figure 12:
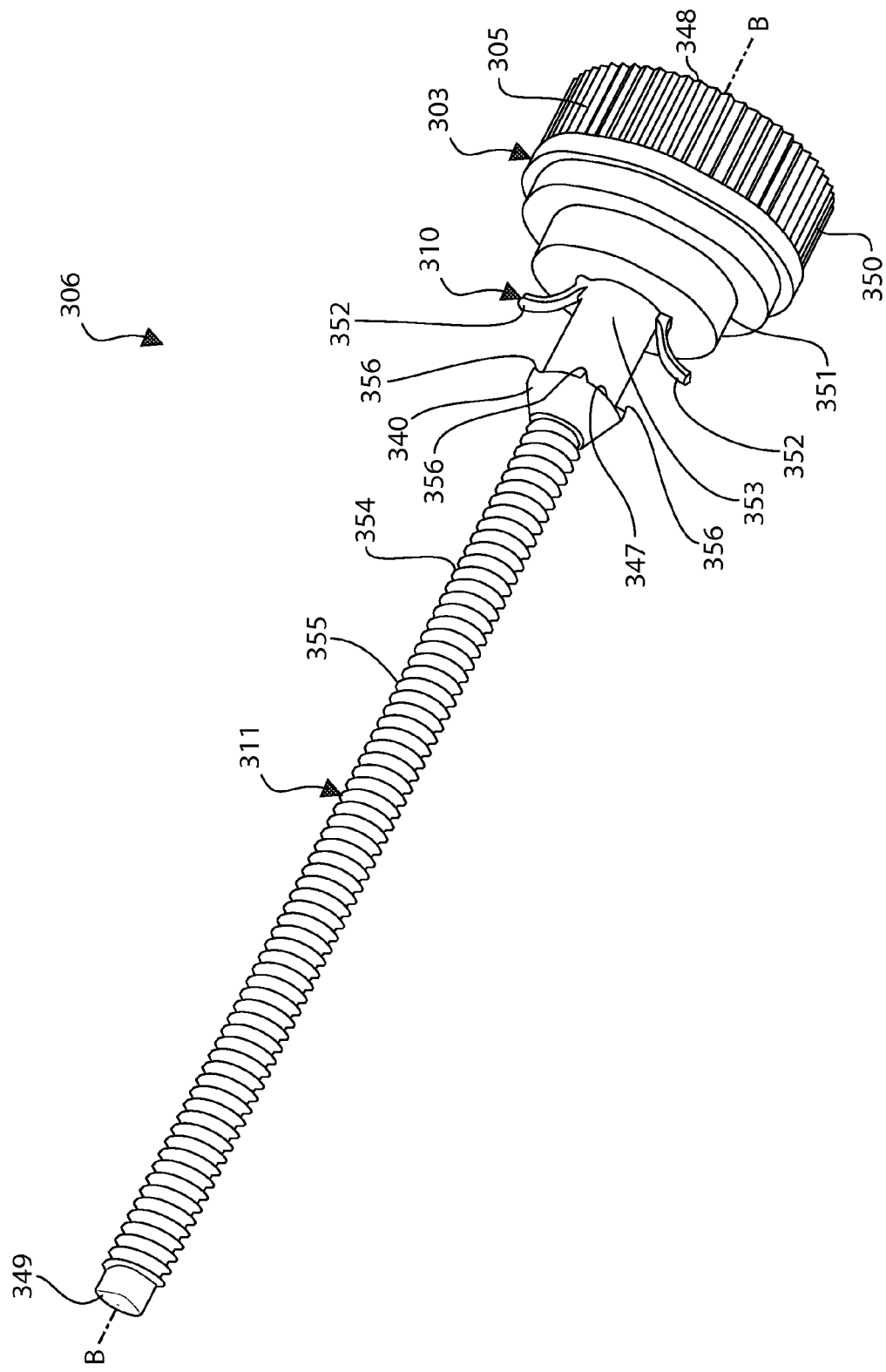
FIG. 12 is a perspective view of the reciprocator of the fluid dispenser of FIG. 3.
Figure 13:
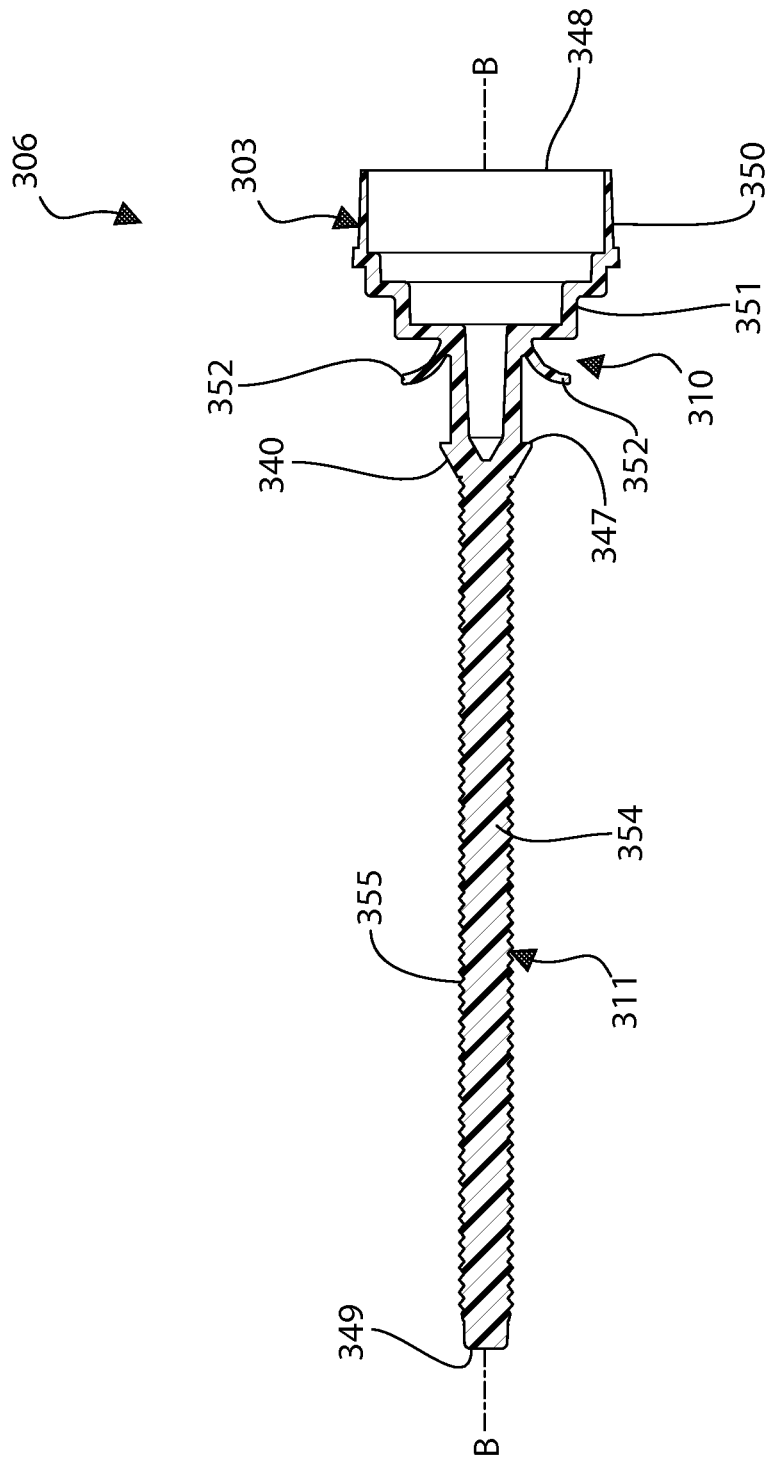
FIG. 13 is a longitudinal cross-sectional view of the reciprocator of the fluid dispenser of FIG. 3.

Referring now to FIGS. 6 and 12-13 concurrently, the reciprocator 306 will be explained in greater detail. As mentioned above, the reciprocator 306 generally comprises the actuator 303, the resilient member 310 and the drive screw 311 and, in certain embodiments, is a unitary integrally formed structure. The reciprocator 306 is constructed of a material that is sufficiently rigid to provide the necessary structural integrity to perform the functions discussed below. In one embodiment, the reciprocator 306 can be formed of a moldable hard plastic. Suitable hard plastics include polymers and copolymers of ethylene, propylene, butadiene, vinyl compounds and polyesters such as polyethylene terephthalate.

The reciprocator 306 extends from a proximal end 348 to a distal end 349 along the longitudinal axis B-B. As mentioned above, the reciprocator 306 comprises the actuator 303 which is located at the proximal end 349 of the reciprocator 306. The actuator 303 comprises a dial portion 350 and a plug portion 351. The dial portion 350 comprises the ridges/ribs 305 and provides the gripping section of the actuator 303 by which the user can rotate the reciprocator 306 with respect to the housing 301. When the dispenser 300 is assembled the dial portion 350 of the actuator 303 protrudes axially beyond the proximal end 315 of the housing 301 while the plug portion 351 of the actuator 303 nests within the collar 332.

The resilient member 310 is located axially between the actuator 303 and the drive screw 311. In the exemplified embodiment, the resilient member 310 is of the leaf-spring type. More specifically, in the exemplified embodiment, the resilient member 310 is formed by a plurality of curved prongs 352 extending axially from the plug portion 351 along a cylindrical portion 353 of the drive screw 311 and in a manner that diverges from the longitudinal axis B-B. In other embodiments, the resilient member may take on other forms and/or be may be a separable component from the reciprocator 306. For example, in certain embodiments, the reciprocator 306 could be, without limitation, a helical spring, a separable leaf spring, an elastomeric pad, and/or combinations thereof. The function of the resilient member 310 will be described in greater detail below.

The drive screw 311 extends axially from the plug portion 351 of the actuator 303 along the longitudinal axis B-B. The drive screw 311 comprises a cylindrical portion 353, a flanged base portion 340 and a threaded portion 354. The cylindrical portion 353 extends axially from the plug portion 351 of the actuator 303 to the flanged base portion 340 and has a smooth outer surface. The threaded portion 354 extends axially from the flanged base portion 340 to the distal end 349 of the reciprocator 306 and comprises a helical ridge 355 extending from the outer surface. The pitch of the helical ridge 355 is selected so that the elevator 308 axially advances toward the dispensing orifice 319 a desired distance upon the drive screw 311 being rotated a predetermined rotational angle, thereby dispensing a pre-selected volume of the fluid from the reservoir 317.

The flanged base portion 340 of the drive screw 311 flares radially outward from the longitudinal axis B-B terminating in lower cam surface 347. In certain other embodiments, such as the one shown in FIGS. 17-19B, the flanged base portion 340C of the drive screw 311C does not flare radially outward from the longitudinal axis B-B, but rather extends radially outward from the longitudinal axis B-B in a more stepped manner. Furthermore, as exemplified in the embodiment of FIGS. 17-19B, the drive screw 311C may further comprises a stopper plate 390C located on the opposite of the flanged base portion 340C than the threaded portion 354C. The stopper plate 390C extends radially outward from the longitudinal axis B-B and will abut the shoulder portion 341C of the collar 332C to prevent over-insertion of the reciprocator 306C into the collar 332C. Such over-insertion of the reciprocator 306C into the collar 332C could damage the resilient member 310C due to over-flexion.

The lower cam surface 347 comprises a plurality of cams 356 extending axially from the lower cam surface 347. In the exemplified embodiment, the cams 356 are saw-toothed protuberances having inclined surfaces 357 that terminate at an apex 358 (FIG. 16B). Of course, the cams 356 can take on a variety different shapes, such as contoured, etc. The lower cam surface 347 is an undulating transverse surface in the exemplified embodiment. The lower cam surface 347 of the reciprocator 306 mates with the upper cam surface 339 when the dispenser 300 is assembled.

When the dispenser 300 is assembled, the reciprocator 306 is rotatable with respect to the housing 301. The drive screw 311 of the reciprocator 306 extends through the axial passageway 335 of the collar 332 and into the chamber 318 of the internal cavity 314. More specifically, the cylindrical portion 353 of the drive screw 311 extends through the neck portion 338 of the collar 332. The flanged base portion 340 is located beyond the neck portion 338 of the collar 332 so that the upper cam surface 339 of the collar 332 is aligned and in contact with the lower cam surface 347 of the reciprocator 306. The resilient member 310, in the form of the prongs 352, is compressed against the inner surface 334 of the shoulder portion 341 of the collar 332, thereby biasing the lower cam surface 347 of the reciprocator 306 downward and into mating surface contact with the upper cam surface 339 of the collar 332. However, the mating surface contact between the upper and lower cam surfaces 339, 347 prevents the reciprocator 306 from being uncoupled from the housing 301. In the exemplified embodiment, the resilient member 310 (in the form of the prongs 352) exerts an axial force on the reciprocator 306 in a second axial direction along the longitudinal axis B-B (i.e., in a direction moving from the distal end 316 to the proximal end 315 of the housing 301).

Figure 8:
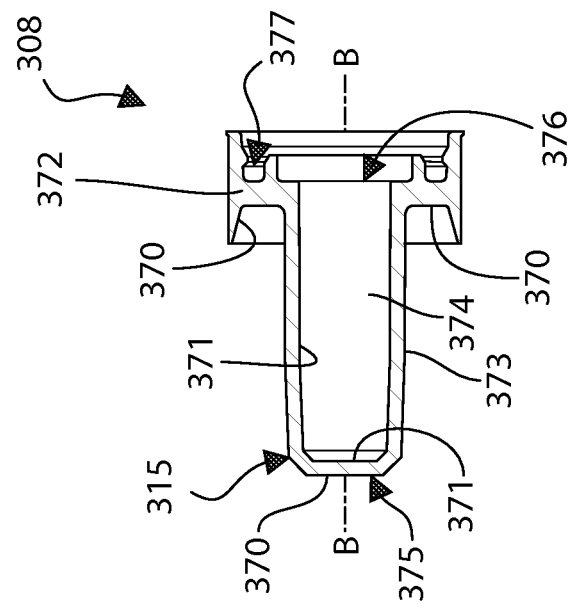
FIG. 8 is a longitudinal cross-sectional view of the elevator of the fluid dispenser of FIG. 3.
Figure 7:
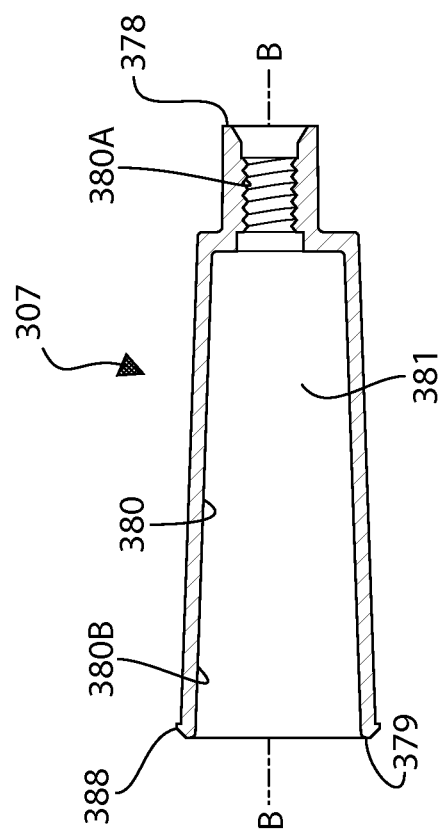
FIG. 7 is a longitudinal cross-sectional view of the extension member of the fluid dispenser of FIG. 3.

Referring now to FIGS. 6 and 7-8 concurrently, the elevator 308 and extension member 307 will be described in greater detail. The elevator 308 is disposed within the internal cavity 314 of the housing 301, thereby dividing the internal cavity 314 into a reservoir 317 and a chamber 318. The reservoir 317 contains the desired fluid or product, which can be any active or inactive oral care agent. The oral care agent and/or its carrier may be in any form such as a solid or a flowable material including without limitation viscous pastes/gels or less viscous liquid compositions. The fluid is a flowable material having a low viscosity in certain embodiments. Any suitable fluid can be used in the present invention. For example, the fluid may include oral care agent such as whitening agents, including without limitation, peroxide containing tooth whitening compositions. Suitable peroxide containing tooth whitening compositions are disclosed in U.S. patent Ser. No. 11/403,372, filed Apr. 13, 2006, to the present assignee, the entirety of which is hereby incorporated by reference. While a tooth whitening agent and a sensitivity agent are the exemplified active agents in the present invention, any other suitable oral care agents can be used with embodiments of the present invention and, thus, stored within the reservoir 317. Contemplated fluids include oral care agents that can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The fluid in one embodiment is free of (i.e., is not) toothpaste. Instead, the fluid is intended to provide supplemental oral care benefits in addition to merely brushing one's teeth. Other suitable oral care fluids could include lip balm or other materials that are typically available in a semi-solid state.

In some embodiments, the materials useful in the oral care fluid contained in the reservoir may include oral care compositions comprising a basic amino acid in free or salt form. In one embodiment, the basic amino acid may be arginine. Various formulations would be useful to supply the arginine to the user. One such oral care composition, e.g., a dentifrice, may be used comprising:
  i. an effective amount of a basic amino acid, in free or salt form, e.g., arginine, e.g., present in an amount of at least about 1%, for example about 1 to about 30%; by weight of total formulation, weight calculated as free base;
  ii. an effective amount of fluoride, e.g., a soluble fluoride salt, e.g., sodium fluoride, stannous fluoride or sodium monofluorophosphate, providing from about 250 to about 25,000 ppm fluoride ions, e.g., about 1,000 to about 1,500 ppm; and
  iii. an abrasive, e.g., silica, calcium carbonate or dicalcium phosphate.

The dental treatment materials of the present invention may have a viscosity suitable for use in tooth treatment applications and methods. As used herein, the "viscosity" shall refer to "dynamic viscosity" and is defined as the ratio of the shearing stress to the rate of deformation as measured by AR 1000-N Rheometer from TA Instruments, New Castle, Del.

When measured at a shear rate of 1 seconds $^{-1}$, the viscosity may have a range with the lower end of the range generally about 0.0025 poise, about 0.1 poise, and more specifically about 75 poise, with the upper end of the range being selected independently of the lower end of the range and generally about 10,000 poise, specifically about 5,000 poise, and more specifically about 1,000 poise. Non-limiting examples of suitable viscosity ranges when measured at a shear rate of 1 seconds $^{-1}$ includes, about 0.0025 poise to about 10,000 poise, about 0.1 poise to about 5,000 poise, about 75 poise to about 1000 poise, and about 0.1 poise to about 10,000 poise.

When measured at a shear rate of 100 seconds $^{-1}$, the viscosity will have a range with the lower end of the range generally about 0.0025 poise, specifically about 0.05 poise, and more specifically about 7.5 poise, with the upper end of the range being selected independently of the lower end of the range and generally about 1,000 poise, specifically about 100 poise, and more specifically about 75 poise. Non-limiting examples of suitable viscosity ranges when measured at a shear rate of 100 seconds.sup.31 1 includes, about 0.0025 poise to about 1,000 poise, about 0.05 poise to about 100 poise, about 7.5 poise to about 75 poise, and about 0.05 poise to about 1,000 poise.

When measured at a shear rate of 10,000 seconds $^{-1}$, the viscosity will have a range with the lower end of the range generally about 0.0025 poise, specifically about 0.05 poise, and more specifically about 5 poise, with the upper end of the range being selected independently of the lower end of the range and generally about 500 poise, specifically about 50 poise. Non-limiting examples of suitable viscosity ranges when measured at a shear rate of 10,000 seconds $^{-1}$ includes, about 0.0025 poise to about 500 poise, about 0.05 poise to about 50 poise, about 5 poise to about 50 poise, and about 0.05 poise to about 500 poise.

Each of the formulations contains a viscosity agent that adjusts the viscosity of the formulation to a level which permits effective flow from the reservoir 317, through the dispensing orifice 319, and out of the aperture 361 of the applicator 309. This agent may be water, thickeners or thinners. The viscosity should be adjusted in relationship to the dimensions of the dispensing orifice 319 (including length, internal transverse cross-sectional area, shape, etc.), the composition of the applicator or other delivery channel used (i.e., hollow channel, porous channel, etc.), and the amount of force available to pressurize the reservoir 317.

The elevator 308 forms a hermetic seal between the reservoir 317 and the chamber 318. An outer surface 370 of the elevator 308 forms a lower end wall of the reservoir 317 while an inner surface 371 of the elevator 308 forms the upper end wall of the chamber 318. The outer surface 370 of the elevator forms a continuous and uninterrupted fluid boundary that bounds a lower end of the reservoir 317. The drive screw 311 does not protrude through the elevator 308, nor through the outer surface 370, and extend into the reservoir 317. Thought of another way, the drive screw 311 is completely isolated from the reservoir 317 and never comes into contact with the fluid within the reservoir 317, even when the elevator 308 is in a fully refracted state (as shown in FIG. 6).

The elevator 308 comprises a base portion 372 and a plug portion 373 extending axially from the base portion 372 along the longitudinal axis B-B toward the dispensing orifice 319. The plug portion 373 comprises an internal cavity 374 having a closed top end 375 and an open bottom end 376. When the dispenser 300 is assembled, and the elevator 308 is in a fully retracted position (as shown in FIG. 6), a distal portion of the drive screw 311 nests within the internal cavity 374 of the plug portion 373 of the elevator 308. However, as can be seen, the drive screw 311 still does not penetrate through the elevator 308 or its outer surface 370. Furthermore, the outer surface 370 of the elevator 308 can comprise more than one surface (as shown in FIG. 8). When the elevator is axially advanced through the reservoir 317 and reaches a fully extended position (not illustrated) in which the reservoir 317 has been substantially emptied of the fluid, the plug portion 373 of the elevator 308 nests within the section 317A of the reservoir 317 having the reduced transverse cross-section.

The elevator 308 is non-rotatable with respect to the housing 301 but can be axially translated relative thereto. Relative rotation between the elevator 308 and the housing 301 can be prevented by designing the elevator 308 and the cavity 317 to have corresponding non-circular transverse cross-sectional shapes. Alternatively, in embodiments where circular transverse cross-sections are desired, the elevator 308 and the inner surface of the housing 301 could be provides with an interlocking groove/ridge cooperation that prevents relative rotation while allowing axial translation. In still another embodiment, such as the one exemplified in FIGS. 17-19B, relative rotation between the elevator 308C and the housing 301C can be prevented by connecting an anti-rotation sleeve 395C to the elevator 308C. The anti-rotation sleeve 395C is non-rotatable with respect to the housing 301C as a result of an interlocking groove/ridge cooperation that is achieved between the inner surface of the housing 301C and the anti-rotation sleeve 395C.

The elevator is threadily coupled to the drive screw 311 so that relative rotation between the drive screw 311 and the elevator 308 axially advances the elevator 308 toward the dispensing orifice 319, thereby expelling a volume of the fluid from the reservoir 317. In the exemplified embodiment, the elevator 308 is threadily coupled to the threaded portion 354 of the drive screw 311 via the extension member 307, which will be described in greater detail below. The elevator 308 further comprises an annular groove 377 formed into its inner surface 371 of the base portion 372 for coupling to the extension member 307.

In alternative embodiments, the elevator 308 may be threadily coupled directly to the threaded portion 354 of the drive screw 311, thereby eliminating the extension member 307. However, the extension member 307 may be preferred in some embodiments so that the elevator 308 does not have to be penetrated by the drive screw 311 while still affording an adequate distance of axial displacement of the elevator 308.

In the exemplified embodiment, the extension member 307 is a tubular sleeve structure that extends from a proximal end 378 to a distal end 379. However, in certain other embodiments, the extension member may be in the form of a frame, struts, or one or more elongate rods extending from a threaded collar to the elevator 308. The extension member 307 has an inner surface 380 that forms an axial passageway 381 that extends through the entirety of the extension member 307. The inner surface 380 comprises a threaded portion 380A and a non-threaded portion 380B. The threaded portion 380A is located at the proximal end 378 of the extension member 307 and comprises a threaded surface that operably mates with the threaded surface of the drive screw 311 when the dispenser 300 is assembled. Further, when the dispenser is assembled, and the elevator 308 is in the full retracted position (as shown in FIG. 6), the drive screw 311 extends through the entirety of the axial passageway 380 of the extension member 380.

The distal end 379 of the extension member 307 comprises a flange 388. The elevator 308 is coupled to the extension member 307 through insertion of the distal end 379 and flange 388 of the extension member 307 into the annular groove 377 of the elevator 308. Of course, the coupling between the elevator 308 and the extension member 307 can be effectuated in a variety of different ways, none of which are limiting of the present invention. Furthermore, in certain embodiments, the elevator 308 and the extension member 307 may be integrally formed as a unitary structure, rather than as separate components.

Figure 16A:
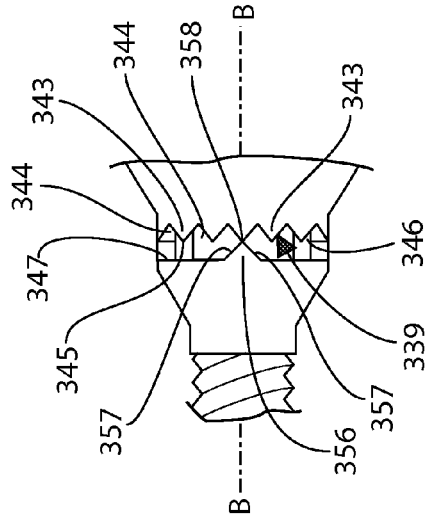
FIG. 16A is a close-up schematic of the cam surfaces of the fluid dispenser of FIG. 3 that cause reciprocation of the elevator, immediately following refraction.
Figure 16B:
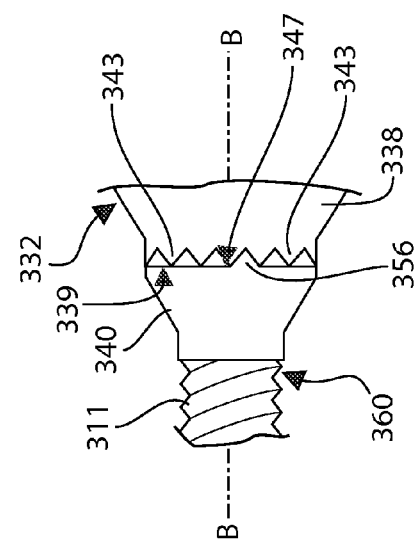
FIG. 16B is a close-up schematic of the cam surfaces of the fluid dispenser of FIG. 16A, immediately prior to retraction.
Figure 17:
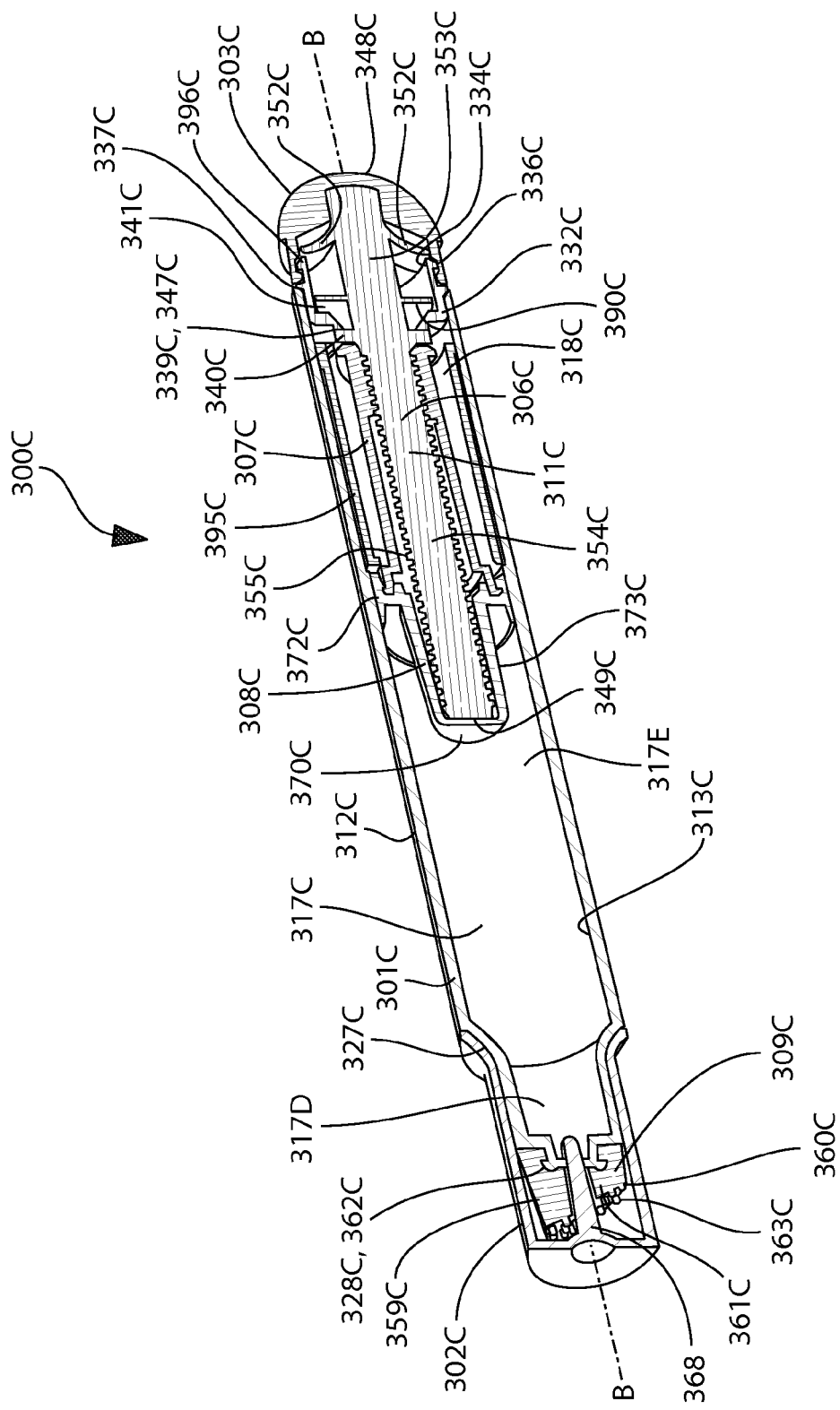
FIG. 17 is a longitudinal cross-sectional view of a fluid dispenser according to a second embodiment of the present invention that can incorporated into the oral care system of FIG. 1.
Figure 18:
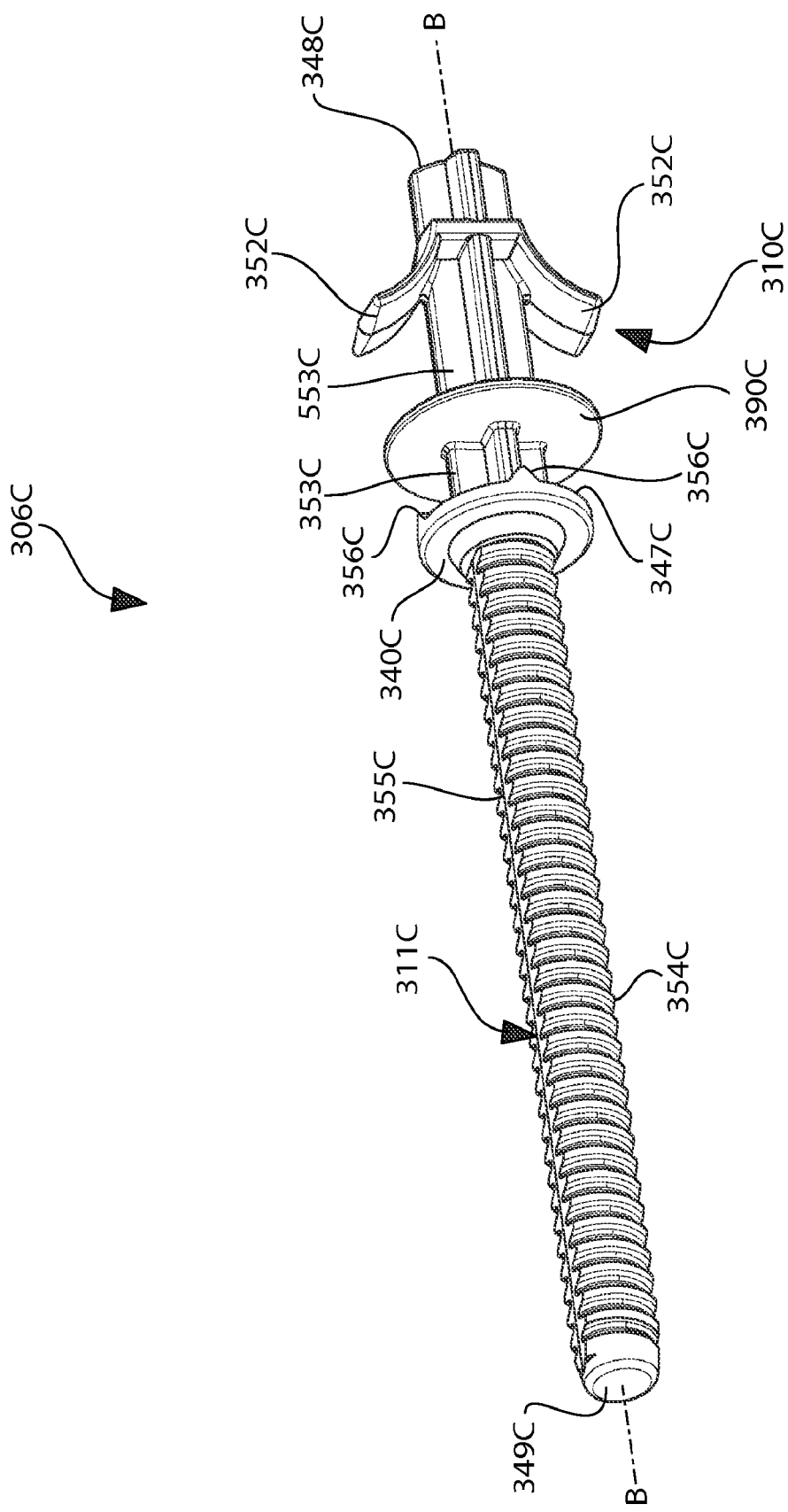
FIG. 18 is a perspective view of the reciprocator of the fluid dispenser of FIG. 17.
Figure 19A:
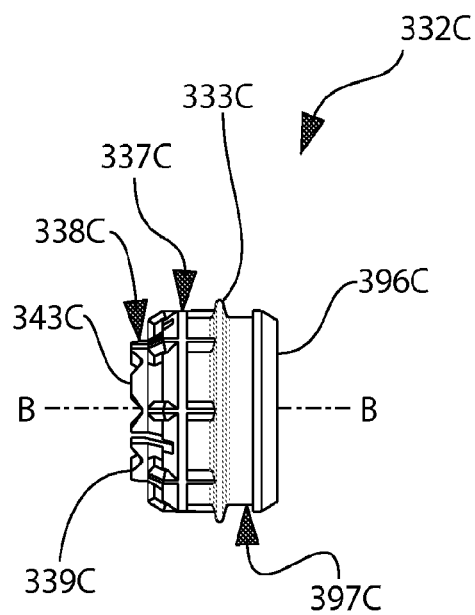
FIG. 19A is a perspective view of the collar of the fluid dispenser of FIG. 17.
Figure 19B:
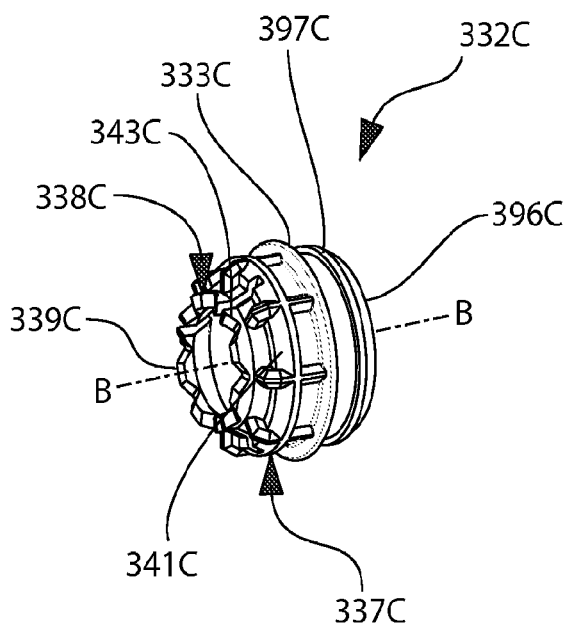
FIG. 19B is a side view of the collar of the fluid dispenser of FIG. 17.

Referring now to FIGS. 6 and 16A-16B concurrently, the mechanism of action that the dispenser 300 uses to dispense the fluid from the reservoir 317 while eliminating weeping will be described. As known to those skilled in the art, axially advancing the elevator 308, which extends throughout the entire transverse cross section of the reservoir 317, while only relieving the fluid through the orifice 319, will result in residual pressure in the reservoir, thereby causing the fluid to weep. To prevent this weeping effect, the dispenser 300 axially retracts the elevator 308, in a reciprocating cycle after each predetermined increment of forward axial advancement of the elevator 308. This is Specifically, when the actuator 303 is rotated, the drive screw 311 is also rotated. Rotation of the drive screw 311 causes the elevator 308 to axially advance a distance in a first axial direction along the longitudinal axis B-B (i.e., in a direction moving from the proximal end 315 to the distal end 316 of the housing 301) due to the relative rotation between the extension member 307 and the drive screw 311, which are threadily coupled together as described above. Of course, in embodiments where the extension member 307 is omitted, said axial advancement will be caused by relative rotation between the elevator 308 and the drive screw 311, which would be threadily coupled directly together or through the use of an intermediary structure. However, in addition to the axial advancement of the elevator 308 imparted by the aforementioned threaded coupling and relative rotation, the elevator is also subjected to an axial translational reciprocation due to relative rotation between the upper and lower cam surfaces 339, 347 of the collar 332 and the reciprocator 306.

As mentioned above, the upper cam surface 339 is non-rotatable with respect to the housing 301. However, when the actuator 303 is rotated, the lower cam surface 347 of the reciprocator 306 also rotates. The relative rotation between the cam surfaces 339, 347 results in the cams 356 of the lower cam surface 347 of the reciprocator 306 to ride up the cams 343 of the upper cam surface 339 of the collar 332 until the apexes 358, 345 of the cams 343, 356 are aligned (as shown in FIG. 16B). This riding of the cams 343, 356 imparts a component of translational axial advancement/displacement to the reciprocator 306, which is in turn is transferred to the elevator 308 via its coupling to the drive screw 311. More specifically, as the actuator 303 is rotated in the direction which causes forward axial advancement of the elevator 308 on the feed screw 311, based on the hand of the thread, the ramped surfaces 357 of the cams 356 will ride up the stationary ramped surfaces 344 of the cams 343. The elevator 308 in turn, will receive the forward axial movement of two separate components, the axial advance due to relative rotation between the elevator 308 and the drive screw 311 and the axial advance due to the component of the ramped surfaces 344, 357 oriented in the axial direction. As the apexes 358 of the cams 356 are rotated past the apexes 345 of the cams 343, as shown in FIG. 16A, the reciprocator 306 will retract in an axial direction opposite to the direction of forward advance as the cams 356 are urged back into the depressions 346 by the bias imparted by the resilient member 310. By moving the reciprocator 306 in a direction which is opposite to the forward travel, the elevator 308 retracts from the fluid in the reservoir, and thereby relieves the residual pressure caused by the forward stroke.

It should be apparent that the component of axial displacement, the reciprocator 306, moves in both the forward and rear stroke of the axial reciprocation is equal. It should be noted however, that the net forward advance of the elevator 308 is greater than the retraction, due to the undirectional forward displacement caused by relative rotation of the feed screw 311 and the elevator 308. This net advance provides for dispensation of a predetermined quantity of the fluid.

The magnitude of the refraction necessary to reduce the residual pressure such that weeping of the fluid, or its components, does not take place varies with the thickness and yield pressure of the fluid and area of the orifices 319 relative to the elevator 308 and the reservoir 317.

Furthermore, when the resilient member 310 urges the cam surfaces 339, 347 back into intimate mating contact after the apexes 345, 358 have passed one another (i.e., from the position shown in FIG. 16B to the position shown in FIG. 16A), an audible click is made. This "click" informs the user that the oral care product has been dispensed and allows the user to dispense a precise and reproducible amount of the fluid.

Referring now to FIGS. 17-19B, an alternative embodiment of a fluid dispenser 300C according to a second embodiment of the present invention is exemplified. The fluid dispenser 300C is substantially identical to the fluid dispenser 300 of FIGS. 3-16B in most structural and functional aspects. Thus, in order to avoid redundancy, only those aspects of the fluid dispenser 300C that are different from the fluid dispenser 300 will be described below, with the understanding that the discussion above regarding the fluid dispenser 300 is applicable. Like structural elements of the fluid dispenser 300C and the fluid dispenser 300 will be identified with like reference numerals, with the addition of the alphabetic suffix "C."

In addition to the components discussed above for the fluid dispenser 300, the fluid dispenser 300C further comprises an anti-rotation sleeve 395C to prevent relative rotation between the elevator 308C and the housing 301C during rotation of the actuator 303C. The anti-rotation sleeve 395C is a hollow tubular structure having a first end that is connected to the elevator 308C. While not visible, a plurality of axially extending ridges are provided on the outer surface of the anti-rotation sleeve 390C that mate with axially extending grooves formed in the inner surface 313C of the housing 301C. Thus, when the actuator 303C is rotated, thereby rotating the reciprocator 306C (and its drive screw 311C), the elevator 308C translates axially due to the threaded coupling via the extension sleeve 307C and the elevator 308C being prohibited from rotating relative to the housing 301C by the anti-rotation sleeve 395C. In this manner, the housing 301C and the internal cavity 317C can have a circular transverse cross-sectional shape. While in the exemplified embodiment the anti-rotation sleeve 390C is described as comprising ridges and the inner surface 313C of the housing 301C comprises grooves, it is to be understood that the anti-rotation sleeve 390C could be designed to include the grooves while the inner surface 313C of the housing 301C would comprise the ridges in certain other embodiments. Moreover, in even further embodiments, the ridges could be in the form of simple tangs or protuberances that mate with the axially extending grooves.

A further difference between the fluid dispenser 300 and the fluid dispenser 300C is the structure of the reciprocator 306C. As mentioned above, the actuator 303C of the fluid dispenser 300C is not integrally formed with the reciprocator 306C but is rather a separate component non-rotatably connected to an end of the reciprocator 306C. In this embodiment, the actuator 303C can be formed of a hard plastic or a thermoplastic elastomer. Of course, other materials could be used if desired.

The reciprocator 306C further comprises a stopper plate 390C that extends radially from a post portion 353C of the reciprocator 306C. During assembly, the stopper plate 390C prevents over-insertion of the reciprocator 306C into the collar 332C that may damage the resilient elements 352C by abutting the shoulder 341C of the collar 332C. Moreover, rather than contacting and interacting with the shoulder 341C of the collar 332 to create the bias, the resilient elements 352C of the reciprocator 306C contact and interact with a distal edge 396C of an extending portion 397C of the collar 332C. When assembled, the extending portion 397C of the collar 332C protrudes from the distal end of the housing 301C.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care system comprising:
    a toothbrush; and
    a dispenser detachably coupled to the toothbrush, the dispenser comprising:
        a housing having a longitudinal axis and an internal reservoir for containing a fluid;
        a dispensing orifice in the housing for dispensing the fluid from the reservoir;
        a collar within the housing, the collar comprising an axial passageway and a cam surface, the collar being non-rotatable with respect to the housing;
        a reciprocator comprising an actuator, a drive screw extending through the axial passageway of the collar, and a cam surface, the reciprocator being rotatable with respect to the housing;
        a resilient member that axially biases the cam surface of the reciprocator and the cam surface of the collar into mating contact;
        an elevator forming an end wall of the reservoir, the elevator being non-rotatable with respect to the housing and threadily coupled to the drive screw; and
    wherein rotation of the actuator causes the elevator to (1) axially advance along the drive screw in a first axial direction due to relative rotation between the drive screw and the elevator, and (2) axially reciprocate due to relative rotation between the cam surface of the collar and the cam surface of the reciprocator.

2. The oral care system according to claim 1 wherein the dispenser further comprises an extension member having a first end coupled to the elevator and a second end threadily coupled to the drive screw, the extension member being non-rotatable with respect to the housing and threadily coupling the elevator to the drive screw, and wherein the axial advancement of the elevator along the drive screw is due to relative rotation between the drive screw and the extension member.

3. The oral care system according to claim 1 wherein the drive screw does not penetrate through the elevator to extend into the reservoir when the elevator is in a fully retracted position.

4. The oral care system according to claim 1 wherein the cam surface of the reciprocator is located on a flanged base portion of the drive screw.

5. The oral care system according to claim 1 wherein the mating contact between the cam surface of the reciprocator and the cam surface of the collar prevents the reciprocator from being uncoupled from the housing.

6. The oral care system according to claim 1 wherein the dispenser further comprises an applicator coupled to a distal end of the housing, the applicator comprising an aperture in fluid communication with the dispensing orifice.

7. The oral care system according to claim 6 wherein the applicator is formed of an elastomeric material.

8. The oral care system according to claim 1 wherein the resilient member is positioned between the actuator of the reciprocator and the collar, the resilient member exerting an axial force on the reciprocator in a second axial direction opposite the first axial direction.

9. The oral care system according to claim 1 wherein the resilient member comprises at least one prong extending from the actuator, the prong integrally formed as part of the reciprocator.

10. The oral care system according to claim 1 wherein the actuator, the drive screw, and the resilient member are integrally formed to form the reciprocator.

11. The oral care system according to claim 1 wherein the elevator comprises a base portion and a plug portion protruding from the base portion, a portion of the drive screw nesting within the plug portion of the elevator when the elevator is in a fully retracted position.

12. The oral care system according to claim 11 wherein the plug portion of the elevator extends into a section of the reservoir having a reduced transverse cross-sectional area when the elevator is axially advanced into a fully extended position.

13. The oral care system according to claim 1 wherein the actuator comprises a dial portion protruding axially from a proximal end of the housing.

14. The oral care system according to claim 1 wherein the dispenser further comprises a removable cap coupled to the housing, the removable cap comprising an axial plug that inserts into and seals the dispensing orifice.

15. The oral care system according to claim 1 wherein the dispenser further comprises an anti-rotation sleeve connected to the elevator that prevents the elevator from rotating relative to the housing.

16. The oral care system according to claim 1 wherein the reciprocator further comprises a stopper plate that prevents over-insertion of the reciprocator through the axial passageway of the collar.

17. An oral care system comprising:
a toothbrush; and
a dispenser detachably coupled to the toothbrush, the dispenser comprising:
 a housing forming an internal cavity extending along a longitudinal axis;
 an elevator disposed within the internal cavity that hermetically separates the internal cavity into a reservoir for containing a fluid and a chamber, the elevator comprising an outer surface forming an end wall of the reservoir and an inner surface forming an end wall of the chamber, the elevator being non-rotatable with respect to the housing;
 a dispensing orifice in the housing for dispensing the fluid from the reservoir;
 an actuator;
 a drive screw in the chamber and operably coupled to the actuator, the drive screw and the actuator being rotatable with respect to the housing, wherein the drive screw does not penetrate through the outer surface of the elevator into the reservoir; and
 an extension member having a first end coupled to the elevator and a second end threadily coupled to the drive screw, the extension member being non-rotatable with respect to the housing; and
 wherein rotation of the actuator causes the elevator to axially advance along the drive screw in a first axial direction due to relative rotation between the drive screw and the extension member.

18. The oral care system according to claim 17 wherein the elevator comprises a base portion and a plug portion protruding from the base portion, a portion of the drive screw nesting within the plug portion of the elevator when the elevator is in a fully retracted position.

19. The oral care system according to claim 18 wherein the plug portion of the elevator extends into a section of the reservoir having a reduced transverse cross-section when the elevator is axially advanced into a fully extended position.

20. The oral care system according to claim 17 wherein the elevator comprises an annular groove formed in the inner surface, the first end of the extension member disposed within the annular groove.

21. The oral care system according to claim 17 wherein when the elevator is in a fully retracted position, the second end of the extension member is threadily coupled to a base portion of the drive screw and the elevator covers a distal end of the drive screw.

22. The oral care system according to claim 17 wherein the extension member is a sleeve forming an axial passageway, the drive screw extending through the axial passageway of the extension sleeve.

23. The oral care system according to claim 17 wherein the dispenser further comprises:
 a collar within the housing, the collar comprising an axial passageway and an upper cam surface, the collar being non-rotatable with respect to the housing;
 the drive screw comprising a lower cam surface;
 a resilient member that axially biases the cam surface of the drive screw and the cam surface of the collar into mating contact;
 wherein rotation of the actuator further causes the elevator to axially reciprocate due to relative rotation between the cam surface of the collar and the cam surface of the drive screw.

24. The oral care system according to claim 23 wherein the resilient member is positioned between the actuator of the reciprocator and the collar, the resilient member exerting an axial force on the reciprocator in a second axial direction opposite the first axial direction.

25. The oral care system according to claim 17 wherein the resilient member comprises at least one prong extending from the actuator.

26. The oral care system according to claim 17 wherein the actuator, the drive screw, and the prong are an integrally formed structure.

27. An oral care system comprising:
a toothbrush; and
a dispenser detachably coupled to the toothbrush, the dispenser comprising:
 a housing having a longitudinal axis and an internal reservoir for containing a fluid;
 a dispensing orifice in the housing for dispensing the fluid from the reservoir;
 a first cam surface within the housing, the first cam surface being non-rotatable with respect to the housing;

a reciprocator comprising an actuator, a drive screw, and a second cam surface, the reciprocator being rotatable with respect to the housing;

a resilient member that axially biases the second cam surface and the cam surface of the collar into mating contact, wherein the mating contact between the first cam surface and the second cam surface prevents the reciprocator from being uncoupled from the housing;

an elevator forming an end wall of the reservoir, the elevator being non-rotatable with respect to the housing and threadily coupled to the drive screw;

wherein rotation of the actuator causes the elevator to (1) axially advance along the drive screw in a first axial direction due to relative rotation between the drive screw and the elevator, and (2) axially reciprocate due to relative rotation between the first cam surface and the second cam surface.

28. The oral care system according to claim 27 wherein the dispenser further comprises an extension member having a first end coupled to the elevator and a second end threadily coupled to the drive screw, the extension member being non-rotatable with respect to the housing and threadily coupling the elevator to the drive screw, and wherein the axial advancement of the elevator along the drive screw is due to relative rotation between the drive screw and the extension member.

29. The oral care system according to claim 27 wherein the drive screw does not penetrate through the elevator to extend into the reservoir.

30. The oral care system according to claim 27 wherein the drive screw extends through an axial passageway circumferentially surrounded by the first cam surface, the second cam surface of the reciprocator located on a flanged base portion of the drive screw.

31. The oral care system according to claim 27 wherein the resilient member exerts an axial force on the reciprocator in a second axial direction opposite the first axial direction.

32. The oral care system according to claim 27 wherein the resilient member comprises at least one prong extending from the actuator, the prong integrally formed with the reciprocator.

33. The oral care system according to claim 27 wherein the actuator, the drive screw, and the resilient member are integrally formed to form the reciprocator.

34. An oral care system comprising:

a toothbrush; and a dispenser detachably coupled to the toothbrush, the dispenser comprising:

a housing forming an internal cavity extending along a longitudinal axis;

an elevator disposed within the internal cavity that hermetically separates the internal cavity into a reservoir for containing a fluid and a chamber, the elevator comprising an outer surface forming an end wall of the reservoir and an inner surface forming an end wall of the chamber, the elevator being non-rotatable with respect to the housing;

a dispensing orifice in the housing for dispensing the fluid from the reservoir;

an actuator;

a drive screw in the chamber and operably coupled to the actuator, the drive screw and the actuator being rotatable with respect to the housing, wherein the drive screw does not penetrate through the outer surface of the elevator into the reservoir when the elevator is in a fully retracted position; and the elevator operbaly coupled to the drive screw so that rotation of the actuator causes the elevator to axially advance along the drive screw in a first axial direction due to relative rotation between the drive screw and the elevator.

* * * * *